(12) United States Patent
Usui et al.

(10) Patent No.: US 7,060,814 B2
(45) Date of Patent: *Jun. 13, 2006

(54) PROBE FOR CONSTRUCTING PROBE-POLYMER METHOD OF CONSTRUCTING PROBE-POLYMER AND UTILIZATION THEREOF

(75) Inventors: Mitsugu Usui, Abiko (JP); Chikako Hakii, Kashiwa (JP); Mari Mitsuka, Kashiwa (JP)

(73) Assignee: Sanko Junyaku Co., Ltd., Tokyo (JP)

( * ) Notice: Subject to any disclaimer, the term of this patent is extended or adjusted under 35 U.S.C. 154(b) by 408 days.

This patent is subject to a terminal disclaimer.

(21) Appl. No.: 09/979,999
(22) PCT Filed: May 28, 2001
(86) PCT No.: PCT/JP01/02554
§ 371 (c)(1),
(2), (4) Date: Nov. 29, 2001
(87) PCT Pub. No.: WO01/75157
PCT Pub. Date: Oct. 11, 2001

(65) Prior Publication Data
US 2003/0008294 A1 Jan. 9, 2003

(30) Foreign Application Priority Data
Mar. 31, 2000 (JP) ............... 2000-098797

(51) Int. Cl.
*C07H 21/04* (2006.01)
*C12Q 1/68* (2006.01)
(52) U.S. Cl. .............. 536/24.3; 536/23.1; 435/6; 435/91.1

(58) Field of Classification Search ............ 435/6; 536/23.1, 24.3
See application file for complete search history.

(56) References Cited

U.S. PATENT DOCUMENTS
4,851,331 A * 7/1989 Vary et al. ............ 435/6
(Continued)

FOREIGN PATENT DOCUMENTS
CA  1 260 372   9/1989
(Continued)

OTHER PUBLICATIONS
T. Notomi et al., "Loop-mediated isothermal amplification of DNA", Nucleic Acid Research, vol. 28, No. 12, (2000).
(Continued)

Primary Examiner—Jehanne Sitton
(74) Attorney, Agent, or Firm—Wenderoth, Lind & Ponackm L.L.P.

(57) ABSTRACT

The present invention provides a method for measuring a target gene under isothermal conditions without using enzyme. A pair of probes each having n (n≧3) base sequence regions complementary to each other are hybridized alternately to form a double-stranded probe-polymer. A base pair at branched sites of each complementary base sequence region is designed to be a G (guanine)-C (cytosine) bond, whereby a stable double-stranded probe-polymer is formed. One of complementary portions in one probe is constituted to have a base sequence complementary to a part of a target gene, whereby a target gene-probe-polymer complex is formed and the target gene is measured.

7 Claims, 39 Drawing Sheets

U.S. PATENT DOCUMENTS

| | | | |
|---|---|---|---|
| 4,882,269 A * | 11/1989 | Schneider et al. | 435/6 |
| 4,894,325 A * | 1/1990 | Englehardt et al. | 435/6 |
| 4,895,325 A | 1/1990 | LeVoir | 246/473.1 |
| 5,175,270 A * | 12/1992 | Nilsen et al. | 536/24.32 |
| 5,216,143 A * | 6/1993 | Hogan et al. | 536/24.32 |
| 5,232,831 A * | 8/1993 | Milliman et al. | 435/6 |
| 5,288,609 A | 2/1994 | Engelhardt et al. | 435/6 |
| 5,437,977 A * | 8/1995 | Segev | 435/6 |
| 5,484,904 A * | 1/1996 | Nilsen et al. | 536/23.1 |
| 5,561,043 A * | 10/1996 | Cantor et al. | 435/6 |
| 5,695,936 A * | 12/1997 | Mandrand et al. | 435/6 |
| 5,853,993 A * | 12/1998 | Dellinger et al. | 435/6 |
| 6,261,846 B1 * | 7/2001 | Usui | 436/94 |
| 6,274,723 B1 * | 8/2001 | Nilsen | 536/24.3 |
| 6,277,607 B1 * | 8/2001 | Tyagi et al. | 435/91.2 |
| 2003/0087262 A1 * | 5/2003 | Usui et al. | 435/6 |

FOREIGN PATENT DOCUMENTS

| | | |
|---|---|---|
| CA | 1309932 | 11/1992 |
| EP | 0 159 719 B1 | 10/1985 |
| EP | 0328829 B1 | 8/1989 |
| EP | 0439182 A2 * | 7/1991 |
| EP | 1 002 877 | 5/2000 |
| EP | 1 002 877 A2 | 5/2000 |
| JP | 2560003 | 11/1985 |
| JP | 01211500 A | 8/1989 |
| JP | 10337186 A | 12/1998 |
| JP | 2000201687 A | 7/2000 |
| WO | 88/02785 | 4/1988 |

OTHER PUBLICATIONS

XP-002304954, L. Stryer, "Molecular Design of Life," *Biochemistry*, Fourth Edition, p. 86, part 1, 1995.

* cited by examiner

FIG. 1

No. 1 probe - SEQ. ID NO: 33

5'-<u>TgC Cgg ACC AgC gAg Cgg</u> · <u>TAg CAg gAT CCC TCT AAg</u> · <u>CTT ATT CAg TAT CgA gTA</u> -3'

$X_1$ region        $X_2$ region        $X_3$ region

No. 2 probe - SEQ. ID NO: 34

3'-<u>gAA TAA gTC ATA gCT CAT</u> · <u>ATC gTC CTA ggg AgA TTC</u> · <u>ACg gCC Tgg TCg CTC gCC</u>-5'

$X'_3$ region        $X'_2$ region        $X'_1$ region

FIG. 7

No. 3 probe  SEQ. ID NO: 13

5'- CGGGTCCTTTCTTGG - CATCACAACCCAGCG - TTCCTGACCAGCGAG - TAGCAGGATCCCTCT -3'
     $X_1$ region           $X_2$ region           $X_3$ region           $X_4$ region

No. 4 probe  SEQ. ID NO: 14

5'- CCAAGAAAGGACCCG - CGCTGGGTTGTGATG - CTCGCTGGTCAGGAA - AGAGGGATCCTGCTA -3'
     $X'_1$ region          $X'_2$ region          $X'_3$ region          $X'_4$ region A case where the number of complementary portions in HoneyComb probes is 4.

How to put $X_1$, $X_2$, $X_3$ and $X_4$ is not limited to the drawn sequence.

FIG. 10

No. 5 probe

SEQ. ID NO: 15

5'- CGGGTCCTTCTTGG - CATCACAACCCAGCG - TTCCTGACCAGCGAG
        $X_1$ region              $X_2$ region              $X_3$ region -TAGCAGGATCCCCTCT - CTTATTCAGTATCGA -3'
        $X_4$ region              $X_5$ region

No. 6 probe

SEQ. ID NO: 16

5'- CCAAGAAAGGACCCG - CGCTGGGTTGTGATG - CTCGCTGGTCAGGAA
        $X'_1$ region             $X'_2$ region             $X'_3$ region -AGAGGGATCCTGCTA - TCGATACTGAATAAG -3'
        $X'_4$ region             $X'_5$ region A case where the number of complementary portions in HoneyComb probes is 6.

A case where the number of complementary portions in HoneyComb probes is n.

FIG. 15
Hydrogen bond between base pairs
of a double-stranded oligonucleotide
(a)
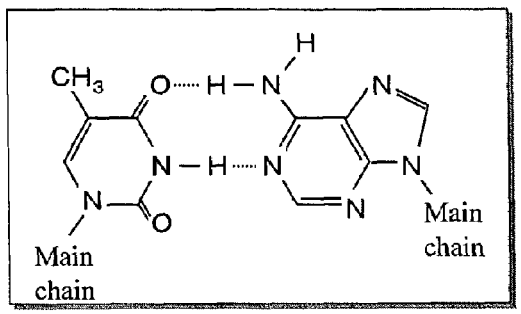
(b)
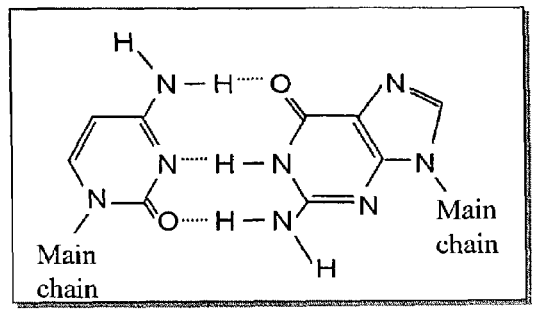
(c)
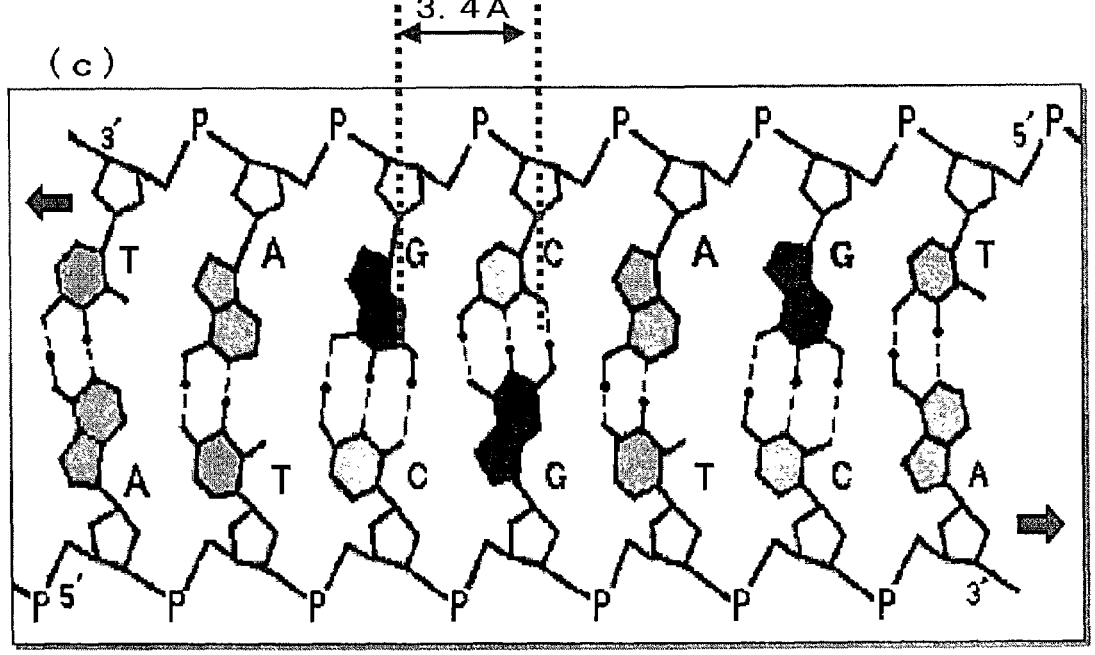

FIG. 16

Nearest—Neighbor Thermodynamic Parameters.

Table 1: Nearest-Neighbor Thermodynamic Parameters for Watson—Crick Base Pair Formation in 1 M NaCl[a]

| propagation sequence | $\Delta H°$ (kcal/mol) | $\Delta S°$ (eu) | $\Delta G°_{37}$ (kcal/mol) |
|---|---|---|---|
| AA/TT | −7.9 ± 0.2 | −22.2 ± 0.8 | −1.00 ± 0.01 |
| AT/TA | −7.2 ± 0.7 | −20.4 ± 2.4 | −0.88 ± 0.04 |
| TA/AT | −7.2 ± 0.9 | −21.3 ± 2.4 | −0.58 ± 0.06 |
| CA/GT | −8.5 ± 0.6 | −22.7 ± 2.0 | −1.45 ± 0.06 |
| GT/CA | −8.4 ± 0.5 | −22.4 ± 2.0 | −1.44 ± 0.04 |
| CT/GA | −7.8 ± 0.6 | −21.0 ± 2.0 | −1.28 ± 0.03 |
| GA/CT | −8.2 ± 0.6 | −22.2 ± 1.7 | −1.30 ± 0.03 |
| CG/GC | −10.6 ± 0.6 | −27.2 ± 2.6 | −2.17 ± 0.05 |
| GC/CG | −9.8 ± 0.4 | −24.4 ± 2.0 | −2.24 ± 0.03 |
| GG/CC | −8.0 ± 0.9 | −19.9 ± 1.8 | −1.84 ± 0.04 |
| init. w/term. G–C[b] | 0.1 ± 1.1 | −2.8 ± 0.2 | 0.98 ± 0.05 |
| init. w/term. A–T[b] | 2.3 ± 1.3 | 4.1 ± 0.2 | 1.03 ± 0.05 |
| symmetry correciton | 0 | −1.4 | 0.4 |

[a] Errors are resampling standard deviations (see text). [b] See text for how to apply the initiation parameters.

Hatim T. Allawi and John SantaLucia, Jr (1997) Biochemistry 36, 10581-10594.

FIG. 17
Stabilization of polymer formation by the stacking effect
(a)
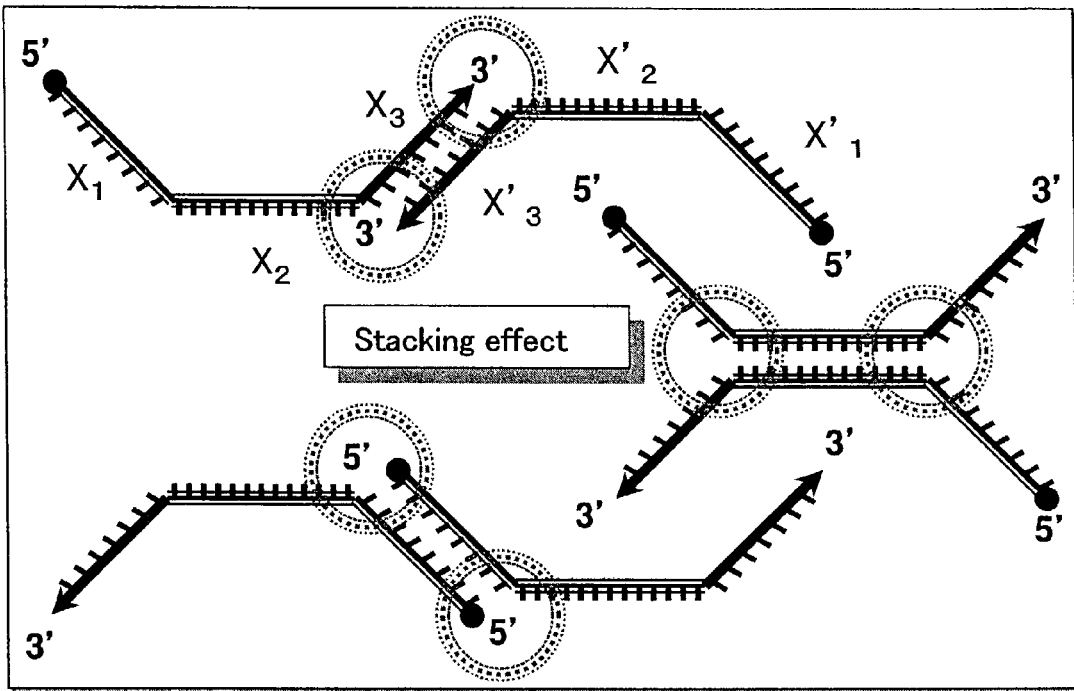
(b)
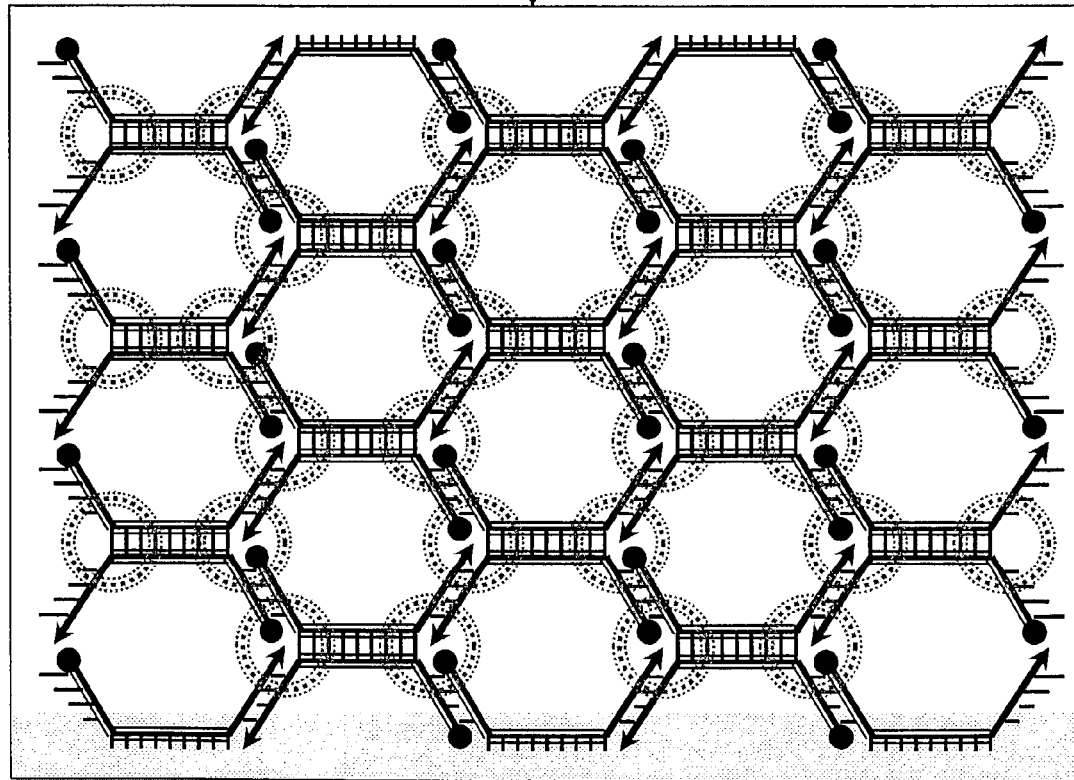

**Synthesis of HCP by the use of the stacking effect
(where one or more bases were replaced)**

FIG. 20

(No. 11 probe) SEQ. ID NO: 35

5'-TgA CTT ACT TAA CCg gTA AAA CAT · AAg CAg gAT CCT CTA AgC CTg A · CgA AgT ACA gTC Cgg Tgg Tg-3'

X₁ region (24 bases)           X₂ region (22 bases)           X₃ region (20 bases)

(No. 12 probe) SEQ. ID NO: 36

3'-gCT TCA TgT CAg gCC ACC AC · TTC gTC CTA ggA gAT TCg gAc T · ACT gAA TgA ATT ggC CAT TTT gTA-5'

X'₃ region (20 bases)           X'₂ region (22 bases)           X'₁ region (24 bases)

FIG. 22

(No. 13 probe) SEQ. ID NO: 3

5'— TgC CgA CC gg CgA gCg · TAg CAT gg CC CTC TAg · CTT ATC gg CC TCg AgA — 3'

(No. 14 probe) SEQ. ID NO: 4

3'— gAA TAg CC gg AgC TCT · ATC gTA CC gg gAg ATC · ACg gCT gg CC gCT CgC — 5'

FIG. 27

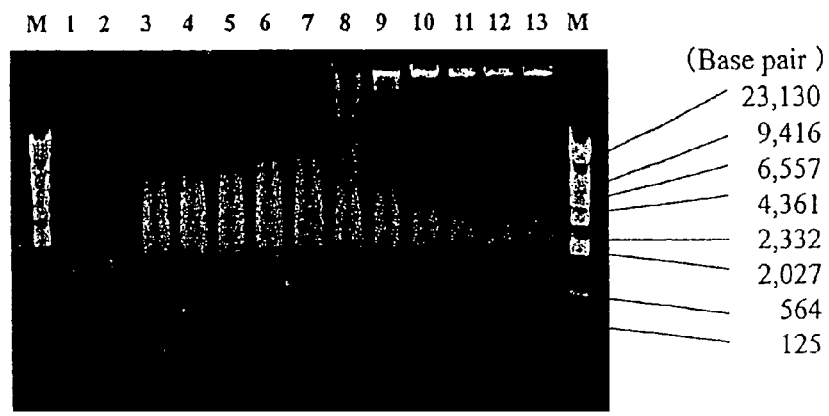

Agarose gel concentration: 0.5 %
M: DNA size marker (λ-Hind III digest)
 1: Probe 1 only
 2: Probe 2 only
 3: A pair of polymerization probes polymerized at a hybridization temperature of 50 °C.
 4: A pair of polymerization probes polymerized at a hybridization temperature of 52 °C.
 5: A pair of polymerization probes polymerized at a hybridization temperature of 54 °C.
 6: A pair of polymerization probes polymerized at a hybridization temperature of 56 °C.
 7: A pair of polymerization probes polymerized at a hybridization temperature of 58 °C.
 8: A pair of polymerization probes polymerized at a hybridization temperature of 60 °C.
 9: A pair of polymerization probes polymerized at a hybridization temperature of 62 °C.
10: A pair of polymerization probes polymerized at a hybridization temperature of 64 °C.
11: A pair of polymerization probes polymerized at a hybridization temperature of 66 °C.
12: A pair of polymerization probes polymerized at a hybridization temperature of 68 °C.
13: A pair of polymerization probes polymerized at a hybridization temperature of 70 °C.

Agarose gel concentration: 2.0 %
M1: DNA size marker (1 kb DNA Ladder)
M2: DNA size marker (50 kb DNA Ladder)
1: Probe 3 only
2: Probe 4 only
3: A pair of polymerized polymerization probes
4: A pair of polymerized polymerization probes cleaved with restriction enzyme Hae III

| $10^2$ | $10^1$ | Reference | | | | | |
|---|---|---|---|---|---|---|---|
| $10^{10}$ | $10^9$ | $10^8$ | $10^7$ | $10^6$ | $10^5$ | $10^4$ | $10^3$ |
| A | B | C | D | E | F | G | H |

$10^{10} \sim 10^1$ : Amount of HCV-RNA (number of copies)

← Reaction temperature (°C)

← Reaction temperature (°C)

FIG. 32
Synthesis of HCP by the use of the stacking effect
HCP-1
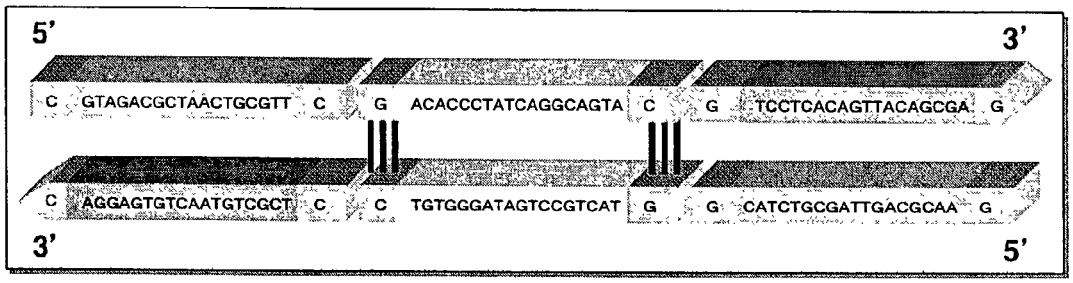
HCP-2
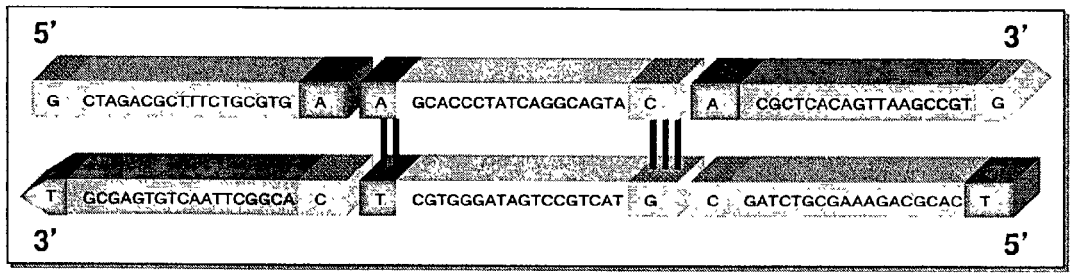
HCP-3
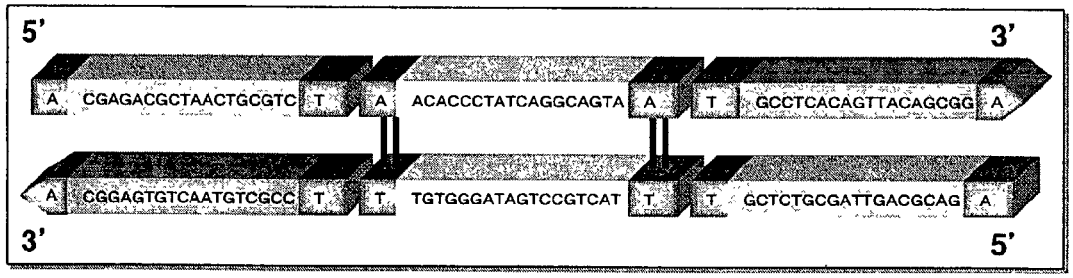

Formation of a polymer from HCP by the use of the stacking effect

Influence of reaction temperature on polymer formation 0.5% agarose gel

Formation of a polymer from HCP by the use of the stacking effect

Influence of reaction time on polymer formation 0.5% agarose gel

Formation of a polymer from HCP by the use of the stacking effect

Influence of HCP concentration on polymer formation

Formation of a polymer from HCP by the use of the stacking effect

Influence of HCP concentration on polymer formation 0.5% agarose gel

Photochemical change of ultraviolet rays to the polymer

Detection of the polymer by ultraviolet absorption

FIG. 38
Photochemical change of the fluorescent material to the polymer
Detection of the polymer having the fluorescent material intercalated therein
(a)
| HCP-3(AT/AT) | |
|---|---|
| reaction time(hr.) | fluorescence intensity |
| 0 | 5692 |
| 0.5 | 5824 |
| 1 | 6387 |
| 3 | 7317 |
| 5 | 8272 |
| 16 | 19208 |
n = 3
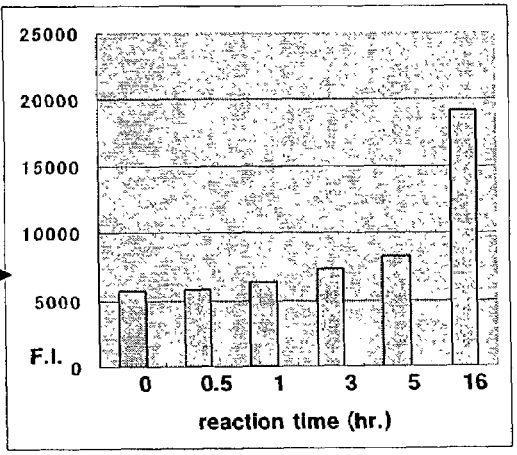
(b)
| HCP-2(AT/GC) | |
|---|---|
| reaction time(hr.) | fluorescence intensity |
| 0 | 5568 |
| 0.5 | 6944 |
| 1 | 8113 |
| 3 | 9490 |
| 5 | 12771 |
| 16 | 22363 |
n = 3
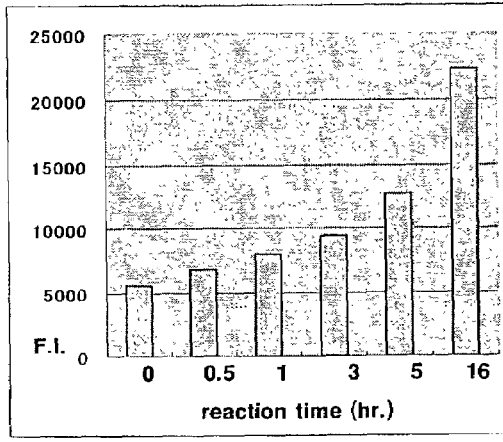
(c)
| HCP-1(GC/GC) | |
|---|---|
| reaction time(hr.) | fluorescence intensity |
| 0 | 5798 |
| 0.5 | 7929 |
| 1 | 8764 |
| 3 | 11541 |
| 5 | 13898 |
| 16 | 19522 |
n = 3
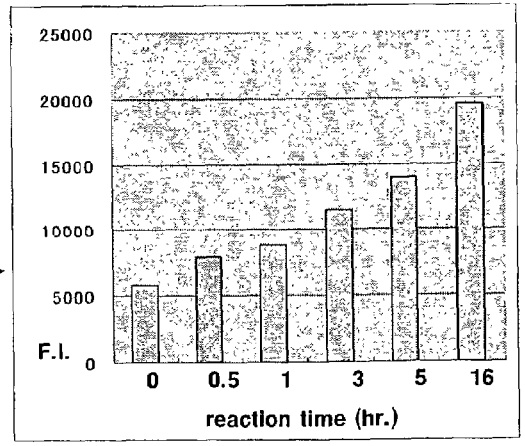

Photochemical change of the fluorescent material to the polymer

Synthesis of HCP by the use of the stacking effect (where one base was replaced)

SEQUENCE LISTING

<160> NUMBER OF SEQ ID NOS: 36

<210> SEQ ID NO 1
<211> LENGTH: 66
<212> TYPE: DNA
<213> ORGANISM: Artificial Sequence
<220> FEATURE:
<223> OTHER INFORMATION: Description of Artificial Sequence: synthesized
      probe 1

<400> SEQUENCE: 1
tgacttactt aaccggaaac ataagcagga tcctctaagc ctgacgaagt atttaacggt      60
ggtatg                                                                66

<210> SEQ ID NO 2
<211> LENGTH: 66
<212> TYPE: DNA
<213> ORGANISM: Artificial Sequence
<220> FEATURE:
<223> OTHER INFORMATION: Description of Artificial Sequence: synthesized
      probe 2

<400> SEQUENCE: 2
atgtttccgg ttaagtaagt catcaggctt agaggatcct gcttcatacc accgttaaat     60
acttcg                                                                66

<210> SEQ ID NO 3
<211> LENGTH: 48
<212> TYPE: DNA
<213> ORGANISM: Artificial Sequence
<220> FEATURE:
<223> OTHER INFORMATION: Description of Artificial Sequence: synthesized
      probe 3

<400> SEQUENCE: 3
tgccgaccgg cgagcgtagc atggccctct agcttatcgg cctcgaga                  48

<210> SEQ ID NO 4
<211> LENGTH: 48
<212> TYPE: DNA
<213> ORGANISM: Artificial Sequence
<220> FEATURE:
<223> OTHER INFORMATION: Description of Artificial Sequence: synthesized
      probe 4

<400> SEQUENCE: 4
cgctcgccgg tcggcactag agggccatgc tatctcgagg ccgataag                  48

<210> SEQ ID NO 5
<211> LENGTH: 45
<212> TYPE: DNA
<213> ORGANISM: Artificial Sequence
<220> FEATURE:

```
<221> NAME/KEY: misc feature
<222> LOCATION: (1)
<223> OTHER INFORMATION: phosphoric acid attached at the 5' end
<220> FEATURE:
<223> OTHER INFORMATION: Description of Artificial Sequence: synthesized
      probe A

<400> SEQUENCE: 5
tagagcgtgc agatagtcga tcctcacagg ggagtgattc atggt              45

<210> SEQ ID NO 6
<211> LENGTH: 45
<212> TYPE: DNA
<213> ORGANISM: Artificial Sequence
<220> FEATURE:
<221> NAME/KEY: misc feature
<222> LOCATION: (1)
<223> OTHER INFORMATION: biotin label attached at the 5' end
<220> FEATURE:
<223> OTHER INFORMATION: Description of Artificial Sequence: synthesized
      probe B

<400> SEQUENCE: 6
tagagcgtgc agatagtcga tcctcacagg ggagtgattc atggt              45

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence: synthesized
      probe C

<400> SEQUENCE: 7
tactcgatac tgaataagcc tcacagggga gtgattcat                     39

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: synthesized
      probe D

<400> SEQUENCE: 8
tactcgatac tgaataaggt tgatccaaga aaggacccg                     39

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence: synthesized
      probe E

<400> SEQUENCE: 9
tactcgatac tgaataagcc tttcgcgacc caacactac                     39

<210> SEQ ID NO 10
<211> LENGTH: 54
<212> TYPE: DNA
<213> ORGANISM: Artificial Sequence
<220> FEATURE:
<223> OTHER INFORMATION: Description of Artificial Sequence: synthesized
      probe 5

<400> SEQUENCE: 10
cttattcagt atcgagtata gcaggatccc tctaagtgcc ggaccagcga gcgg     54
```

<210> SEQ ID NO 11
<211> LENGTH: 54
<212> TYPE: DNA
<213> ORGANISM: Artificial Sequence
<220> FEATURE:
<223> OTHER INFORMATION: Description of Artificial Sequence: synthesized
      probe 6

<400> SEQUENCE: 11
tactcgatac tgaataagct tagagggatc ctgctaccgc tcgctggtcc ggca         54

<210> SEQ ID NO 12
<211> LENGTH: 54
<212> TYPE: DNA
<213> ORGANISM: Artificial Sequence
<220> FEATURE:
<221> NAME/KEY: misc feature
<222> LOCATION: (1)
<223> OTHER INFORMATION: biotin label attached at the 5' end
<220> FEATURE:
<223> OTHER INFORMATION: Description of Artificial Sequence: synthesized
      probe 7

<400> SEQUENCE: 12
tactcgatac tgaataagct tagagggatc ctgctaccgc tcgctggtcc ggca         54

<210> SEQ ID NO 13
<211> LENGTH: 60
<212> TYPE: DNA
<213> ORGANISM: Artificial Sequence
<220> FEATURE:
<223> OTHER INFORMATION: Description of Artificial Sequence: synthesized
      probe 8

<400> SEQUENCE: 13
cgggtccttt cttggcatca caacccagcg ttcctgacca gcgagtagca ggatccctct   60

<210> SEQ ID NO 14
<211> LENGTH: 60
<212> TYPE: DNA
<213> ORGANISM: Artificial Sequence
<220> FEATURE:
<223> OTHER INFORMATION: Description of Artificial Sequence: synthesized
      probe 9

<400> SEQUENCE: 14
ccaagaaagg acccgcgctg ggttgtgatg ctcgctggtc aggaaagaag gatcctgcta   60

<210> SEQ ID NO 15
<211> LENGTH: 75
<212> TYPE: DNA
<213> ORGANISM: Artificial Sequence
<220> FEATURE:
<223> OTHER INFORMATION: Description of Artificial Sequence: synthesized
      probe 10

<400> SEQUENCE: 15
cgggtccttt cttggcatca caacccagcg ttcctgacca gcgagtagca ggatccctct   60
cttattcagt atcga                                                   75

<210> SEQ ID NO 16
<211> LENGTH: 75
<212> TYPE: DNA
<213> ORGANISM: Artificial Sequence
<220> FEATURE:
<223> OTHER INFORMATION: Description of Artificial Sequence: synthesized probe 11

<400> SEQUENCE: 16
ccaagaaagg acccgcgctg ggttgtgatg ctcgctggtc aggaaagagg gatcctgcta      60
tcgatactga ataag      75

<210> SEQ ID NO 17
<211> LENGTH: 60
<212> TYPE: DNA
<213> ORGANISM: Artificial Sequence
<220> FEATURE:
<223> OTHER INFORMATION: Description of Artificial Sequence: synthesized
      probe HPL-1-1

<400> SEQUENCE: 17
cgtagacgct aactgcgttc gacaccctat caggcagtac gtcctcacag ttacagcgag      60

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequence: synthesized
      probe HPL-1-2

<400> SEQUENCE: 18
gaacgcagtt agcgtctacg gtactgcctg atagggtgtc ctcgctgtaa ctgtgaggac      60

<210> SEQ ID NO 19
<211> LENGTH: 60
<212> TYPE: DNA
<213> ORGANISM: Artificial Sequence
<220> FEATURE:
<223> OTHER INFORMATION: Description of Artificial Sequence: synthesized
      probe HPL-2-1

<400> SEQUENCE: 19
gctagacgct ttctgcgtga agcaccctat caggcagtac acgttcacag ttaagccgtg      60

<210> SEQ ID NO 20
<211> LENGTH: 60
<212> TYPE: DNA
<213> ORGANISM: Artificial Sequence
<220> FEATURE:
<223> OTHER INFORMATION: Description of Artificial Sequence: synthesized
      probe HPL-2-2

<400> SEQUENCE: 20
tcacgcagaa agcgtctagc gtactgcctg atagggtgct cacggcttaa ctgtgagcgt      60

<210> SEQ ID NO 21
<211> LENGTH: 60
<212> TYPE: DNA
<213> ORGANISM: Artificial Sequence
<220> FEATURE:
<223> OTHER INFORMATION: Description of Artificial Sequence: synthesized
      probe HPL-3-1

<400> SEQUENCE: 21
acgagaccct aactgcgtct aacaccctat caggcagtaa tgcctcacag ttacagcgga      60

<210> SEQ ID NO 22
<211> LENGTH: 60
<212> TYPE: DNA
<213> ORGANISM: Artificial Sequence
<220> FEATURE:

```
<223> OTHER INFORMATION: Description of Artificial Sequence: synthesized
      probe HPL-3-2

<400> SEQUENCE: 22
agacgcagtt agcgtctcgt ttactgcctg atagggtgtt tccgctgtaa ctgtgaggcg    60

<210> SEQ ID NO 23
<211> LENGTH: 60
<212> TYPE: DNA
<213> ORGANISM: Artificial Sequence
<220> FEATURE:
<223> OTHER INFORMATION: Description of Artificial Sequence: synthesized
      probe

<400> SEQUENCE: 23
cctagacgct aactgcgtcc ggaaccctat caggcagtgg ggtcctcaca tacagcgagg    60

<210> SEQ ID NO 24
<211> LENGTH: 60
<212> TYPE: DNA
<213> ORGANISM: Artificial Sequence
<220> FEATURE:
<223> OTHER INFORMATION: Description of Artificial Sequence: synthesized
      probe

<400> SEQUENCE: 24
ggacgcagtt agcgtctagg ccactgcctg ataggttcc cctcgctgta tgtgaggacc     60

<210> SEQ ID NO 25
<211> LENGTH: 60
<212> TYPE: DNA
<213> ORGANISM: Artificial Sequence
<220> FEATURE:
<223> OTHER INFORMATION: Description of Artificial Sequence: synthesized
      probe

<400> SEQUENCE: 25
gctagacgct aactgcgtcg gcaaccctat caggcagtcg cgtcctcaca tacagcgagc    60

<210> SEQ ID NO 26
<211> LENGTH: 60
<212> TYPE: DNA
<213> ORGANISM: Artificial Sequence
<220> FEATURE:
<223> OTHER INFORMATION: Description of Artificial Sequence: synthesized
      probe

<400> SEQUENCE: 26
cgacgcagtt agcgtctagc cgactgcctg atagggttgc gctcgctgta tgtgaggacg    60

<210> SEQ ID NO 27
<211> LENGTH: 60
<212> TYPE: DNA
<213> ORGANISM: Artificial Sequence
<220> FEATURE:
<223> OTHER INFORMATION: Description of Artificial Sequence: synthesized
      probe

<400> SEQUENCE: 27
ccctagacgt aactcgtccc gggaacctat cagcagtggg gggtcctcaa tacaggaggg    60

<210> SEQ ID NO 28
<211> LENGTH: 60
<212> TYPE: DNA
<213> ORGANISM: Artificial Sequence
<220> FEATURE:
<223> OTHER INFORMATION: Description of Artificial Sequence: synthesized
```

```
          probe

<400> SEQUENCE: 28
gggacgagtt acgtctaggg cccactgctg ataggttccc ccctcctgta ttgaggaccc    60

<210> SEQ ID NO 29
<211> LENGTH: 60
<212> TYPE: DNA
<213> ORGANISM: Artificial Sequence
<220> FEATURE:
<223> OTHER INFORMATION: Description of Artificial Sequence: synthesized
      probe

<400> SEQUENCE: 29
ccctagacgt aactcgtccc gcgaacctat cagcagtcgc gggtcctcaa tacaggaggg    60

<210> SEQ ID NO 30
<211> LENGTH: 60
<212> TYPE: DNA
<213> ORGANISM: Artificial Sequence
<220> FEATURE:
<223> OTHER INFORMATION: Description of Artificial Sequence: synthesized
      probe

<400> SEQUENCE: 30
gggacgagtt actgctaggg gcgactgctg ataggttcgc ccctcctgta ttgaggaccc    60

<210> SEQ ID NO 31
<211> LENGTH: 60
<212> TYPE: DNA
<213> ORGANISM: Artificial Sequence
<220> FEATURE:
<223> OTHER INFORMATION: Description of Artificial Sequence: synthesized
      probe

<400> SEQUENCE: 31
ccctagacgt aactcgtccc gcgaacctat cagcagtgcg gggtcctcaa tacaggaggg    60

<210> SEQ ID NO 32
<211> LENGTH: 60
<212> TYPE: DNA
<213> ORGANISM: Artificial Sequence
<220> FEATURE:
<223> OTHER INFORMATION: Description of Artificial Sequence: synthesized
      probe

<400> SEQUENCE: 32
gggacgagtt acgtctaggg cgcactgctg ataggttcgc ccctcctgta ttgaggaccc    60

<210> SEQ ID NO 33
<211> LENGTH: 54
<212> TYPE: DNA
<213> ORGANISM: Artificial Sequence
<220> FEATURE:
<223> OTHER INFORMATION: Description of Artificial Sequence: synthesized
      No. 1 probe

<400> SEQUENCE: 33
tgccggacca gcgagcggta gcaggatccc tctaagctta ttcagtatcg agta          54

<210> SEQ ID NO 34
<211> LENGTH: 54
<212> TYPE: DNA
<213> ORGANISM: Artificial Sequence
<220> FEATURE:
<223> OTHER INFORMATION: Description of Artificial Sequence: synthesized
      No. 2 probe
```

```
<400> SEQUENCE: 34
ccgctcgctg gtccggcact tagagggatc ctgctatact cgatactgaa taag         54

<210> SEQ ID NO 35
<211> LENGTH: 66
<212> TYPE: DNA
<213> ORGANISM: Artificial Sequence
<220> FEATURE:
<223> OTHER INFORMATION: Description of Artificial Sequence: synthesized
      No. 11 probe

<400> SEQUENCE: 35
tgacttactt aaccggtaaa acataagcag gatcctctaa gcctgacgaa gtacagtccg   60
     gtggtg                                                          66

<210> SEQ ID NO 36
<211> LENGTH: 66
<212> TYPE: DNA
<213> ORGANISM: Artificial Sequence
<220> FEATURE:
<223> OTHER INFORMATION: Description of Artificial Sequence: synthesized
      No. 12 probe

<400> SEQUENCE: 36
atgttttacc ggttaagtaa gtcatcaggc ttagaggatc ctgcttcacc accggactgt   60
acttcg                                                              66
```

PROBE FOR CONSTRUCTING PROBE-POLYMER METHOD OF CONSTRUCTING PROBE-POLYMER AND UTILIZATION THEREOF

This application is a 371 of PCT/JP01/02554, filed Mar. 28, 2001.

TECHNICAL FIELD

The present invention relates to a pair of probe-polymer forming probes each composed of n (n≧3) base sequence portions complementary to each other, a method for forming a probe-polymer by the use of the probes, and a method for detecting a target gene by using the above method.

BACKGROUND ART

A method for analyzing DNA in the field of genetic engineering is a very useful means for searching for novel genes and pathogenic genes, and diagnosing genetic diseases, cancer diseases, infectious diseases and so on. As a method for amplification and analysis of a target gene, a polymerase chain reaction (PCR) method is widely used (U.S. Pat. Nos. 4,683,195, 4,683,202). As other means, there are a reverse transcriptase—polymerase chain reaction method (a RT-PCR method, Trends in Biotechnology, 10, 146-152, 1992), a ligase chain reaction method (LCR, EP 320308) and so on. Because these techniques involve steps such as strand separation of double-stranded DNA into single-strands, synthesis of complementary strands from primers, etc., requiring high- and low-temperature reactions to be repeated many times; therefore, a strict temperature controller is required, and a long time for temperature setting causes time losses. Further, the above techniques require an expensive enzyme.

Thereafter, a DNA amplification method under isothermal conditions was developed to solve the problem of temperature control. For example, there are a strand displacement amplification method (SDA, Nucleic Acid Res., 20, 1691–1696, 1992), a nucleic acid sequence based amplification method (NASBA, Nature, 350, 91–92, 1991) and a Qβ replicase method (BioTechnology, 6, 1197–1202, 1988). These methods can be advantageously carried out under isothermal conditions, but need expensive enzymes such as DNA polymerases, restriction endonucleases, etc.

These isothermal nucleic acid amplification methods have some problems in terms of the number of primers and operation, and it is demanded to establish a nucleic acid amplification method and a nucleic acid detection method of simple techniques at low cost without using enzymes.

On the other hand, the amplification of genes by the branched DNA probe method involves previously synthesizing a branched polymer single-stranded DNA probe and hybridizing it to a target gene to detect the target gene. However, the hybridization of the branched polymer single-stranded DNA probe to the target gene takes a long time because the branched DNA probe is a polymer. In addition, the branched polymer single-stranded DNA is limited in size, so that the detection of the target gene is also limited.

In view of the problems described above, the present applicant previously proposed a novel isothermal nucleic acid amplification method (a method for forming a probe-polymer) without using enzymes (EP 1002877A). This proposed method makes use of a pair of probes each composed of three portions (HoneyComb Probe, referred to hereinafter as HCP), and the three portions in the first probe are composed of base sequences complementary to each other, and the base sequences of both the probes are designed such that upon reaction, the three regions in one probe hybridize to only such regions in the other probe. By this method, a plurality of pairs of the probes upon reaction can hybridize to each other to form a polymer of the probes (a Probe Alternation Link Self-Assembly Reaction, referred to hereinafter as a PALSAR method).

This proposed method for forming a probe-polymer can be used to detect a target gene in a sample, and realizes an epoch-making, simple and inexpensive technique by isothermal operation without using enzymes.

DISCLOSURE OF THE INVENTION

The present inventors have further investigated the previously proposed method for forming a probe-polymer, in which the probe-polymer was made more stable in the present invention to further improve the technique.

As a result of the inventors' diligent study for solving the problem described above, it has been found that a plurality of pairs of probes each composed of three or more portions complementary to each other are hybridized such that they cross alternately, whereby a double-stranded polymer can be easily formed under isothermal conditions, and further found that in a pair of probes used in the PALSAR method, a base sequence at each of branched sites (both terminals) of each region upon hybridization crossing alternately is designed to be a G (guanine)—C (cytosine) bond, whereby the bond strength between the base pair at the branched site of each region is made stronger than that by an A (adenine)—T (thymine) bond, thus further strengthening the special interaction caused by π electrons of bases in the whole of this region, thus the present invention being completed.

The present invention provides probe-polymer forming probes, a method for forming a probe-polymer by the use of the probes, a probe-polymer formed by the method, a method for measuring a target gene by the use of the probe-polymer and a reagent for detection of a target gene by the use of the probe-polymer, wherein a more stable probe-polymer can be produced by strengthening the bond strength between base pairs at branched sites in each region, the probe can be efficiently polymerized under isothermal conditions to form a probe-polymer without using DNA polymerases or branched DNA, further the stacking of bases in the formed polymer has a regular higher-order structure bringing about a hypochromic effect called "hypochromism" reducing the intensity of an absorption band at 260 nm in the ultraviolet region, whereby the state of the polymer can be confirmed, and furthermore an inexpensive fluorescent material can be inserted between stacked bases of the polymer to cause a change in fluorescence intensity, whereby the state of the polymer can be confirmed, with the result that a target gene can be detected easily at lower cost.

The probe-polymer forming probes according to the present invention comprise, in a first aspect, a pair of first and second probes having the following characteristics (a), (b) and (c):

(a) a pair of the first and second probes each composed of n (n≧3) base sequence regions complementary to each other, wherein an $X_1$ region, an $X_2$ region, an $X_3$ region, ... an $X_n$ region provided in this order from the 5'-terminal of the first probe have base sequences complementary, respectively, to an $X'_1$ region, an $X'_2$ region, an $X'_3$ region, ... an $X'_n$ region provided in this order from the 5'-terminal of the second probe;

(b) when a pair of the first and second probes are reacted with each other, the $X_1$ region hybridizes only to the $X'_1$ region, the $X_2$ region hybridizes only to the $X'_2$ region, the $X_3$ region hybridizes only to the $X'_3$ region, ... and the $X_n$ region hybridizes only to the $X'_n$ region, and when both the probes are bound, they hybridize to each other at any one of the regions in one probe, and a plurality of the pairs of the first and second probes bound at the one region hybridize to each other to form a probe-polymer; and (c) at least one G (guanine) or C (cytosine) is arranged at branched sites of complementary base sequence regions in a pair of the first and second probes, and upon hybridization of a pair of the first and second probes, at least one C—G bond is formed at the terminals of the complementary regions.

The probe-polymer forming method of the present invention comprises polymerizing a plurality of pairs of the first and second probes having the above-described characteristics (a), (b) and (c) to form a probe-polymer.

Further, the present invention comprises arranging G (guanine) or C (cytosine) at branched sites (both terminals) of complementary regions in a pair of the probes used and forming G—C bonds upon hybridization, thereby leading to the special interaction caused by π electrons of bases due to the stacking of bases to form a stable double-stranded polymer.

The probe-polymer of the present invention is obtained by polymerizing a plurality of pairs of the first and second probes having the above-described characteristics (a), (b) and (c).

Further, the present invention covers a method for measuring a trace amount of a target gene in a sample by using the probe-polymer forming method.

The method for measuring a target gene according to the present invention comprises, in a first aspect, the following steps (1), (2) and (3):

(1) with a pair of first and second probes having the above-described characteristics (a), (b) and (c) as polymerization probes, reacting either one of the probes having one base sequence region complementary to a part of a target gene with a sample so as to being the probe to the target gene in the sample;

(2) reacting a plurality of the above polymerization probes with each other to form a target gene-probe-polymer complex; and (3) washing the unreacted probes off from the used polymerization probes and measuring the amount of the formed probe-polymer.

The method for measuring a target gene according to the present invention comprises, in a second aspect, the following steps (1), (2) and (3):

(1) with a pair of first and second probes having the above-described characteristics (a), (b) and (c) as polymerization probes, reacting at least one target gene capture probe with a sample so as to bind the capture probe to a target gene, the target gene capture probe being composed of two regions, one region of which is a base sequence region complementary to a part of the target gene and the other region of which is a base sequence region complementary to one region in either one of the two polymerization probes;

(2) then reacting the polymerization probes with each other so as to bind the capture probe to the polymerization probes to form a target gene-probe-polymer complex; and (3) washing the unreacted probes off from the used polymerization probes and measuring the amount of the formed probe-polymer.

In the method for measuring a target gene according to the present invention, it is preferable that the amount of the probe-polymer is measured by binding a fluorescent material to the probe-polymer to measure the fluorescence resulting from the emission of the fluorescent material or using a change in optical absorption to ultraviolet rays.

The reagent for detecting a target gene according to the present invention comprises, in a first aspect, a pair of the first and second probes having the above-described characteristics (a), (b), (c) and further the following characteristic (d) as polymerization probes and essential elements:

(d) one of complementary base sequence regions in either one of the above-described first or second probe has a region having a base sequence complementary to a part of a target gene.

The reagent for detecting a target gene according to the present invention comprises, in a second aspect, a plurality of pairs of the first and second probes having the above-described characteristics (a), (b) and (c) as polymerization probes; and at least one target gene capture probe composed of at least two regions, one region of which is a base sequence region complementary to a part of a target gene and the other region of which is a base sequence region complementary to one region in either one of the two polymerization probes as essential elements.

The probe-polymer forming probes according to the present invention comprises, in a second aspect, a pair of the first and second probes having the above-described characteristics (a) and (b).

The number (n) of complementary base sequence regions in each of the first and second probes is preferably 3, 4, 5 or 6. The number of bases in each of the complementary base sequence regions is preferably at least 8. The first and second probes are composed of bases selected from DNA, RNA or PNA.

In the present invention, the "complementary base sequence" covers a completely complementary base sequence, including a base sequence capable of hybridization under stringent conditions to form a probe-polymer.

Bases of a pair of the probes in the present invention are constituted such that in three or more complementary base sequence regions, only one region of one probe hybridizes specifically to a corresponding region thereto of the other probe upon one to one hybridization.

FIG. 1 is a schematic diagram showing an example of a pair of DNA probes having three complementary base sequence regions. In FIG. 1, a DNA probe No. 1 has an $X_1$ region, an $X_2$ region and an $X_3$ region, while a DNA probe No. 2 has an $X'_1$ region, an $X'_2$ region and an $X'_3$ region. DNA probes Nos. 1 and 2 are constituted such that when they are hybridized, the $X_1$ region is bound only to the $X'_1$ region, the $X_2$ region is bound only to the $X'_2$ region and the $X_3$ region is bound only to the $X'_3$ region (FIG. 2).

In other words, with a pair of the inventive DNA probes each composed of three portions complementary to each other, when they are hybridized such that they cross alternately, the $X_1$ region is bound only to the $X'_1$ region, the $X_2$ region is bound only to the $X'_2$ region and the $X_3$ region is bound only to the $X'_3$ region as shown in FIG. 2, so that a pair of the probes are hybridized alternately in three binding patters.

Thus, by the use of the probes constituted as mentioned above, the two probes are bound alternately. Concretely, the DNA probe No. 1 and the DNA probe No. 2 are alternately bound in three dimensions to produce a probe-polymer, as illustrated in FIG. 3. Consequently, a plurality of pairs of probes, which have been hybridized alternately in the three binding patterns shown in FIG. 2, can form a double-stranded probe-polymer, one example of which is schematically illustrated in FIG. 3. FIG. 4 illustrates an example of a three-dimensional conceptual structure of the schematic diagram of FIG. 3. FIG. 5 is a schematic diagram illustrating a plurality of pairs of the DNA probes which have been hybridized in different binding patterns from FIG. 3. FIG. 6 illustrates an example of a three-dimensional conceptual structure of the schematic diagram of FIG. 5.

FIG. 7 is a schematic diagram showing one example of a pair of DNA probes composed of four portions complementary to each other. In FIG. 7, a DNA probe No. 3 has an $X_1$ region, an $X_2$ region, an $X_3$ region and an $X_4$ region, while a DNA probe No. 4 has an $X'_1$ region, an $X'_2$ region, an $X'_3$ region and an $X'_4$ region. DNA probes Nos. 3 and 4 are constituted such that when they are hybridized, the $X_1$ region is bound only to the $X'_1$ region, the $X_2$ region is bound only to the $X'_2$ region, the $X_3$ region is bound only to the $X'_3$ region and the $X_4$ region is bound only to the $X'_4$ region (FIG. 8).

In other words, with a pair of the inventive DNA probes each composed of four portions complementary to each other, when they are hybridized such that they cross alternately, the $X_1$ region is bound only to the $X'_1$ region, the $X_2$ region is bound only to the $X'_2$ region, the $X_3$ region is bound only to the $X'_3$ region and the $X_4$ region is bound only to the $X'_4$ region as shown in FIG. 8, so that a pair of the probes are hybridized alternately in four binding patters.

Thus, by the use of the probes constituted as mentioned above, the two probes are bound alternately. Concretely, the DNA probe No. 3 and the DNA probe No. 4 are alternately bound in three dimensions to produce a probe-polymer, as illustrated in FIG. 9.

In the method of hybridizing a pair of probes having 4, 5 and 6 complementary portions to each other as shown in FIGS. 8, 11 and 13, the number of complementary base sequence regions can theoretically be further increased.

FIG. 14 is a schematic diagram showing a further example of a pair of DNA probes each composed of "n" portions (n≧3) complementary to such portions of the other DNA probe. In FIG. 14, a DNA probe No. 9 has an $X_1$ region, an $X_2$ region, an $X_3$ region . . . an $X_{n-1}$ region and an $X_n$ region, while a DNA probe No. 10 has an $X'_1$ region, an $X'_2$ region, an $X'_3$ region, . . . an $X'_{n-1}$ region and an $X'_n$ region.

The DNA probes Nos. 9 and 10 are constituted such that when they are hybridized, the $X_1$ region is bound only to the $X'_1$ region, the $X_2$ region is bound only to the $X'_2$ region, the $X_3$ region is bound only to the $X'_3$ region . . . the $X_{n-1}$ region is bound only to the $X'_{n-1}$ region and the $X_n$ region is bound only to the $X'_n$ region (FIG. 14).

In other words, with a pair of the inventive DNA probes each composed of "n" portions complementary to each other, when they are hybridized such that they cross alternately, the $X_1$ region is bound only to the $X'_1$ region, the $X_2$ region is bound only to the $X'_2$ region, the $X_3$ region is bound only to the $X'_3$ region . . . the $X_{n-1}$ region is bound only to the $X'_{n-1}$ region and the $X_n$ region is bound only to the $X'_n$ region as shown in FIG. 14, so that the pair of probes are hybridized alternately in "n" binding patters.

The same principle of hybridization for the two DNA probes illustrated in FIGS. 8, 11, 13 and 14 applies to hybridization of a DNA probe and an RNA probe, two RNA probes, two PNA probes, a PNA probe and a DNA probe, or a PNA probe and an RNA probe.

The number (n) of complementary base sequence regions in one probe is not particularly limited insofar as a pair of the probes can be polymerized to form a probe-polymer, but "n" is preferably 3 to 5 in consideration of costs and efficiency.

Further, the present invention provides a method for forming a stable double-stranded polymer, wherein in a pair of the probes used in the PALSAR method, a base pair at a branched site of each complementary portion when they hybridize alternately to each other is designed to be a G (guanine)—C (cytosine) bond, thereby leading to the special interaction caused by π electrons of bases due to the stacking of bases to form a stable double-stranded polymer.

Bases are present about the center of the double helix structure of DNA or oligonucleotide in which A (adenine) and T (thymine) or G (guanine) and C (cytosine) are specifically bonded via hydrogen bonds to form a base pair. As is apparent from the results using the nearest-neighbor thermodynamic parameters by Hatim T. Allawi et al. (Biochemistry, 36, 10581–10594, 1997) shown in FIG. 16, the bonding between G and C bound via 3 hydrogen bonds [FIG. 15(b)] is stronger than the bonding between A and T bound via 2 hydrogen bonds [FIG. 15(a)], so that in order to hybridize theoretically at three regions in the PALSAR method as shown in FIG. 17(a) and 17(b), the alternately crossing circled sites of the used plural pairs of probes are bound via G—C bonds to stabilize the polymer formation.

Further, this base pair forms one plane in the form of an almost rectangular plate as a whole, and this plane is arranged at an almost right angle to the double helix axis. Accordingly, the respective base pairs are all arranged in parallel to each other at 3.4 Å intervals [FIG. 15(c)].

Further, with the stacking of bases on these base-pair planes at 3.4 Å intervals, there brings about special interaction attributable to π electrons of bases, and this is a significant factor for stabilization of the double helix structure. Further, it is known that the stacking of bases gives rise to a hypochromic effect called "hypochromism" where the intensity of an absorption band in the ultraviolet region of DNA or oligonucleotide at 260 nm is decreased by 30%.

In the PALSAR method, the inventors have worked out that when the bond strength at branched sites of each region is weak, the hybridization of the region sandwiched by the branched sites is unstabilized; therefore, the effect of the stacking of bases resulting from the special interaction by π electrons of bases in the whole of the region is increased so as to strengthen the hybridization reaction at each region crossed alternately by the PALSAR method.

Further, the stacking of bases in the polymer formed by the PALSAR method has a regular higher-order structure and hence the following methods can be realized: There is generated a hypochromic effect called "hypochromism" causing a decrease in the intensity of an absorption band in the ultraviolet region at 260 nm to confirm the state of the polymer, and further a fluorescent material is inserted between stacked bases of the polymer to cause a change in fluorescence intensity to confirm the state of the polymer.

As shown in FIG. 18, the region where a pair of probes used in the PALSAR method hybridize in crossing alternately to each other has about 20 bases, and it is estimated that the stacking effect is increased by strengthening bonds at the circled branched sites, resulting in stabilization of hybridization of the 20-base region sandwiched by the branched sites.

The number of C or G arranged at each of the branched sites of the above-described complementary region may be at least one base, a plurality of bases being applicable. In consideration of the base sequence of each complementary region, the number of such bases can be suitably selected. If two or more C and G are to be arranged, C and G can be combined arbitrarily and arranged in any order as shown in FIG. 19. Further, if a base sequence complementary to a part of a target gene is used as one region in a probe in the method for detecting a target gene as described below, it is possible to select C or G as a base arranged at the terminal of the complementary region.

By the use of the above-described polymerization probes, a trace amount of a target gene in a sample can be detected. For example, when a base sequence complementary to a part of a target gene is used as one complementary region of a pair of polymerization probes, the probe is reacted with a sample and then with the other pair of probes. Then, the amount of the resulting probe-polymer bound to the target gene is measured, whereby the target gene can be measured.

In an alternative method, the amount of a target gene can be measured in the same manner as described above except for use of a capture probe composed of, e.g., two regions, that is, a region having a base sequence complementary to a part of the target gene and a region having a base sequence complementary to one region of the polymerization probe. At least one kind of capture probes should be used, and plural kinds of capture probes can be used depending on selection of several complementary sites in the target gene.

By this method, a target gene can be not only detected directly but also a target material can be measured indirectly. That is, after a nucleotide is bound to a material for measurement to which a target gene was bound (a target material), the nucleotide can be measured as the target gene in the same manner as described above.

As for the probes described above, the DNA probe is a single-stranded fragment composed of phosphate groups, sugars and bases (adenine, thymine, guanine and cytosine), while the RNA probe is a single-stranded fragment whose bases are adenine, uracil, guanine and cytosine. PNA is identical with DNA and RNA in kinds of bases, but is different in the structure in that the "sugar-phosphate" backbone in DNA is replaced by "N-(2-aminoethyl)glycine derivatives".

The nucleic acid constituting the polymerization probe (HCP) is composed usually of DNA or RNA, but may be a nucleic acid analogue. The nucleic acid analogue includes, for example, peptide nucleic acid (PNA, WO 92/20702). Further, a pair of probes are composed usually of the same type of nucleic acids, but a pair of DNA and RNA probes may be used. That is, the type of nucleic acids in the probes can be selected from DNA, RNA or nucleic acid analogues (e.g., PNA). Furthermore, the nucleic acid composition in one probe is not required to consist of only one kind of nucleic acids (e.g., DNA only), and as necessary, for example, a probe (a chimera probe) composed of DNA and RNA may be usable, which is within the scope of the present invention.

The length of each complementary base sequence region in the probes is at least 5 bases in terms of number of bases, preferably at least 8 bases, more preferably 10 to 100 bases, and most preferably 15 to 30 bases.

These probes can be synthesized in known methods. For example, the DNA probe can be synthesized by the phosphoamidite method by the use of a DNA synthesizer-394 model of Applied Biosystems Inc. Alternative methods include the phosphotriester method, the H-phosphonate method, etc., but any methods can be used for preparing the probes.

BRIEF DESCRIPTION OF THE DRAWINGS

FIG. 1 is a schematic diagram showing an example of a pair of DNA probes.

FIG. 7 is a schematic diagram of an example showing a pair of DNA probes when n is 4.

FIG. 10 is a schematic diagram showing an example of a pair of DNA probes when n is 5.

FIG. 15 is a drawing showing the state of hydrogen bonds between base pairs in a double-stranded oligonucleotide.

FIG. 16 is a table showing the Nearest-Neighbor Thermodynamic Parameters by Hatim T. Allawi et al. (Biochemistry, 36, 10581–10594, 1997).

FIG. 17 is a schematic diagram showing the principle of stabilization of polymer formation by the stacking effect.

FIG. 20 is a schematic diagram showing an example of a pair of DNA probes each composed of portions complementary to each other being different in length.

FIG. 22 is a schematic diagram showing an example of a pair of DNA probes into which portions cleaved with a restriction enzyme are inserted.

FIG. 27 is a photograph showing the results of Example 1.

FIG. 32 is a schematic diagram showing the synthesis of HCP by the use of the stacking effect.

FIG. 38 is a diagram showing cases where each polymer having a fluorescent material intercalated therein was detected by the photochemical change of the fluorescent material to the polymer.

BEST MODE TO CARRY OUT THE INVENTION

In the present invention, with a pair of probes having "$n(n \geq 3)$" base sequence regions complementary to each other both the probes are reacted with each other under isothermal conditions in the absence of enzymes to form a probe-polymer. The number of probes to be used is not particularly limited, but preferably in the range of $10^2$ to $10^{15}$ probes. The composition and concentration of the buffering solution used in the reaction are not particularly limited, and a buffering solution used ordinarily in a nucleic acid amplification technique can be preferably employed. The pH may also be suitable in the common range, preferably in the range of pH 7.0 to pH 9.0. The reaction temperature is 40 to 80° C., preferably 55 to 65° C. These conditions are not particularly limited.

This method for forming a probe-polymer can be applied to detection of a target gene in a sample.

Figure 21:
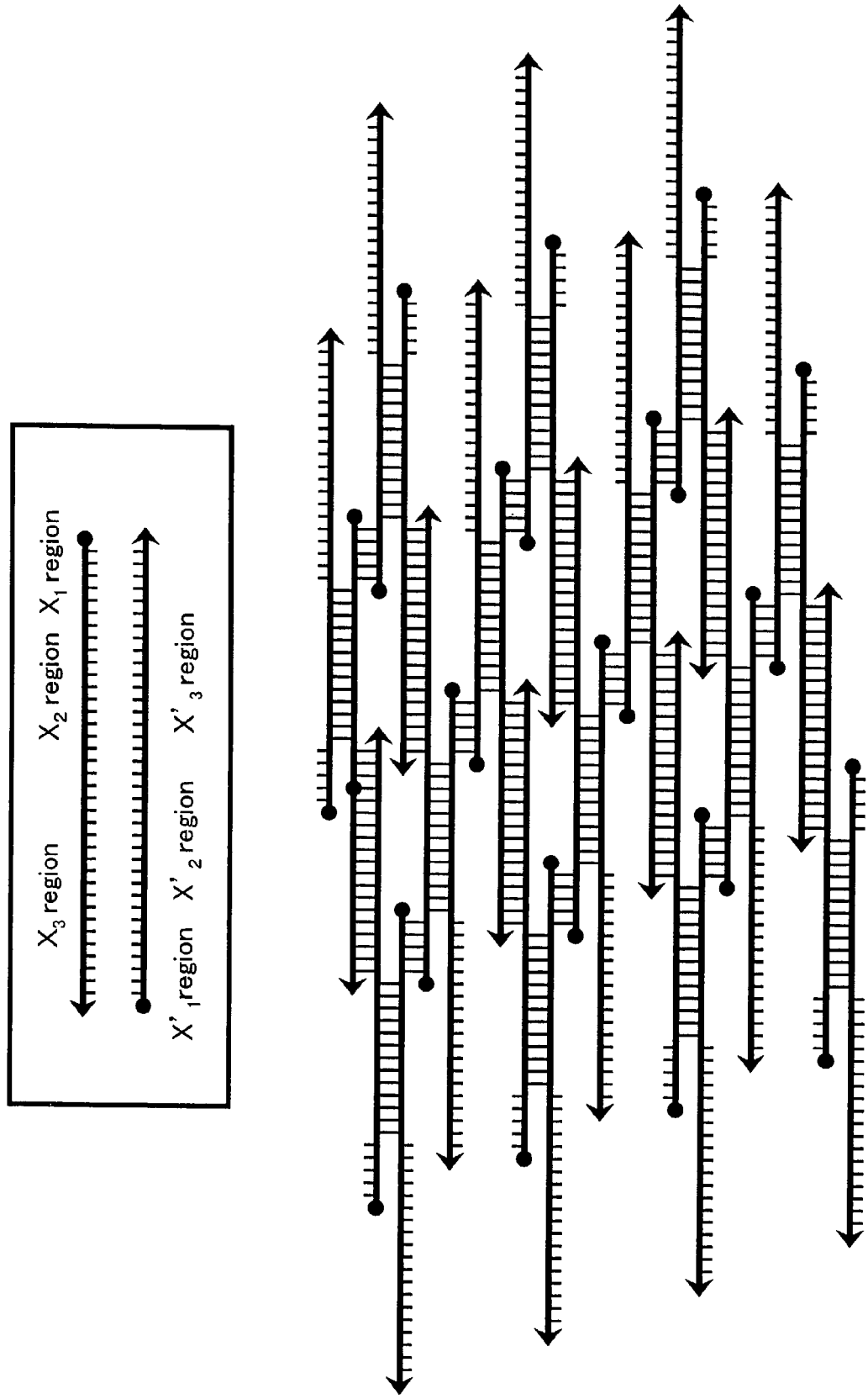
FIG. 21 is a schematic diagram illustrating the formation of a polymer where a pair of DNA probes shown in FIG. 20 hybridize alternately.

Illustrating the constitution of the present invention using a more specific example, the lengths (the number of bases) of complementary base sequence regions in one probe may be the same or different. For example, in the case of DNA probes as shown in FIG. 20, when DNA probes No. 11 and No. 12 are hybridized, an $X_1$ region and an $X'_1$ region hybridize with 24 bases, an $X_2$ region and an $X'_2$ region hybridize with 22 bases, and an $X_3$ region and an $X'_3$ region hybridize with 20 bases to form a probe-polymer (FIG. 21).

Figure 2:
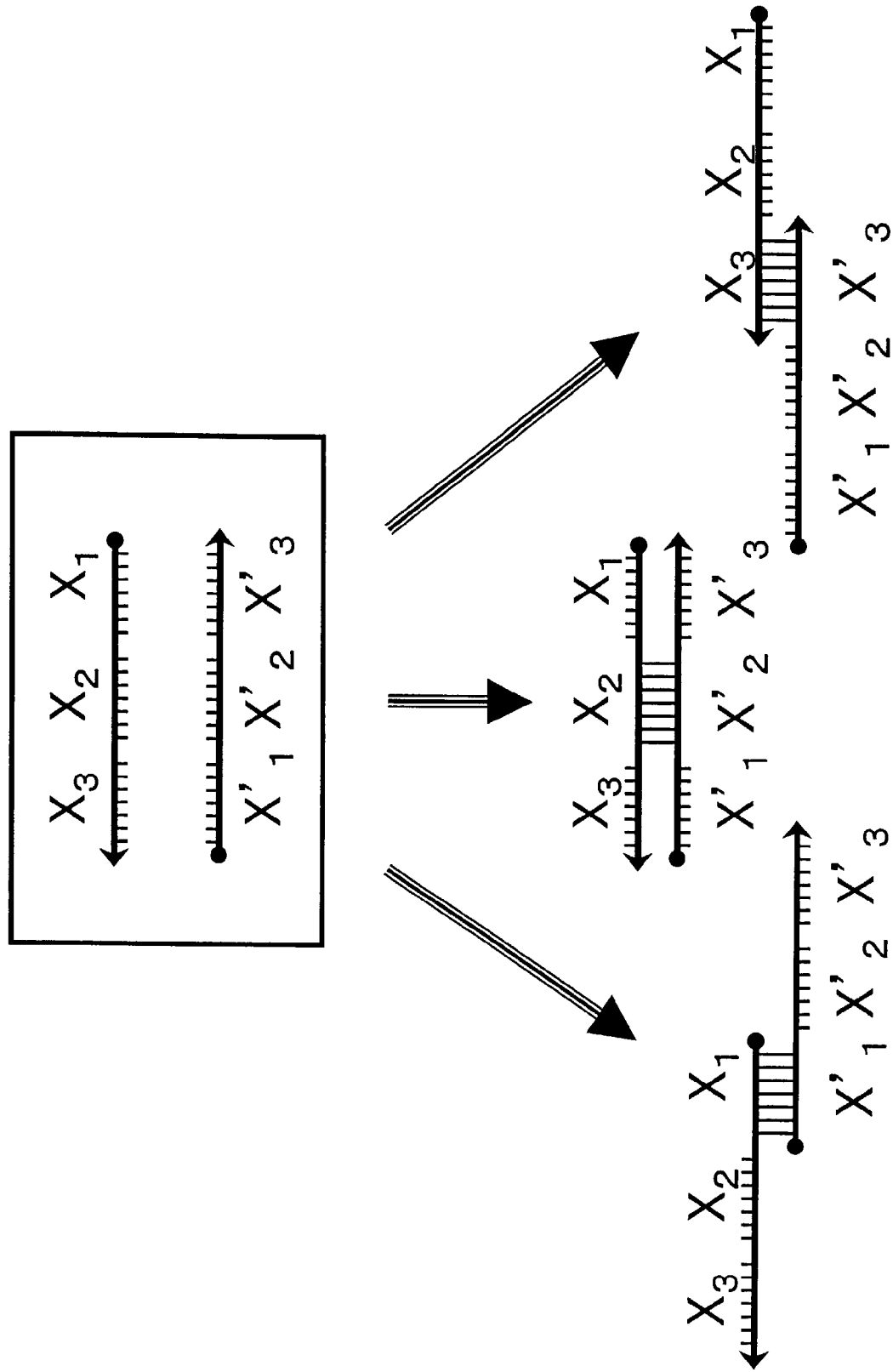
FIG. 2 is a schematic diagram of an example showing how a pair of DNA probes are bound.
Figure 3:
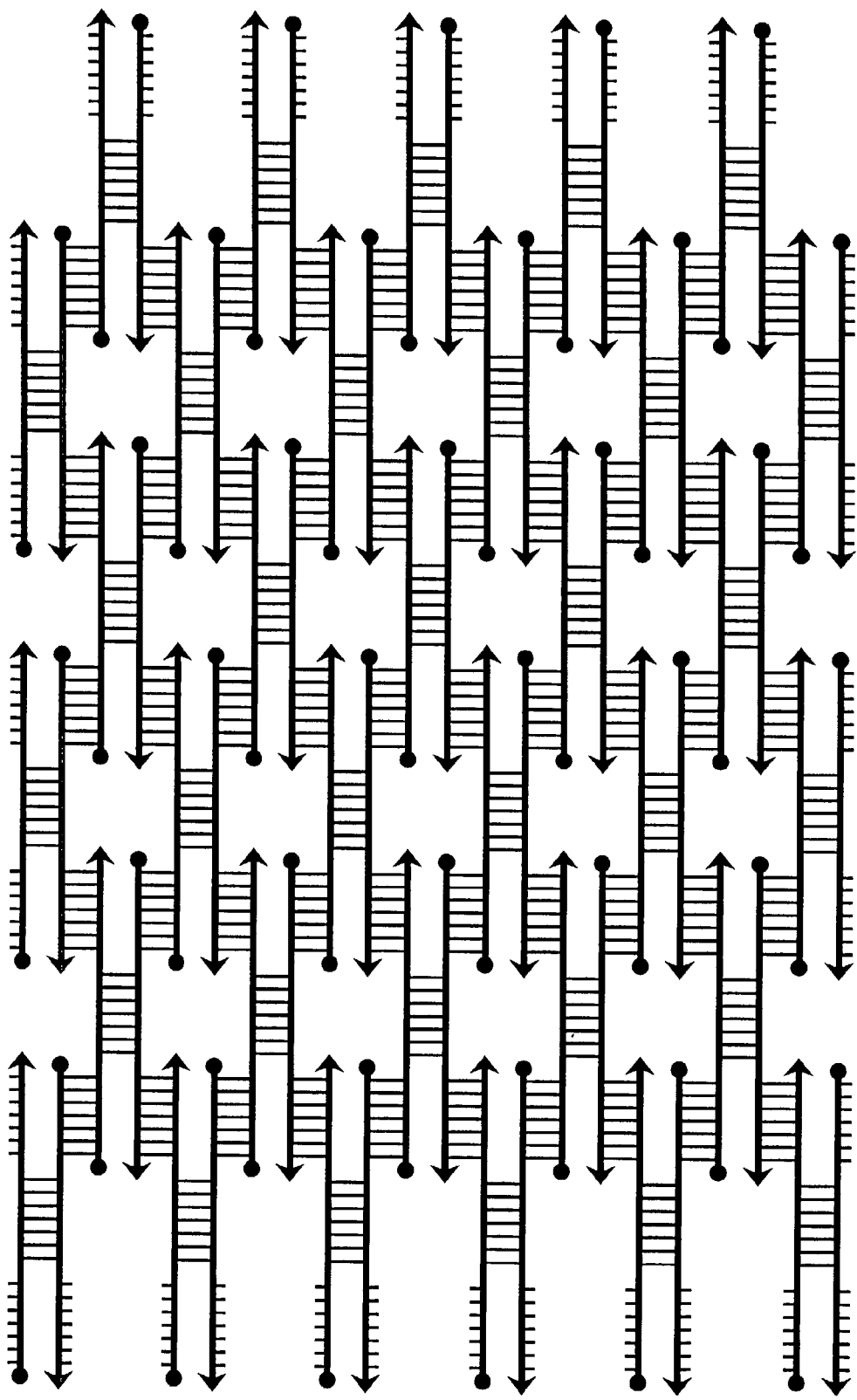
FIG. 3 is a schematic diagram showing the formation of a polymer where a pair of DNA probes hybridize alternately.
Figure 4:
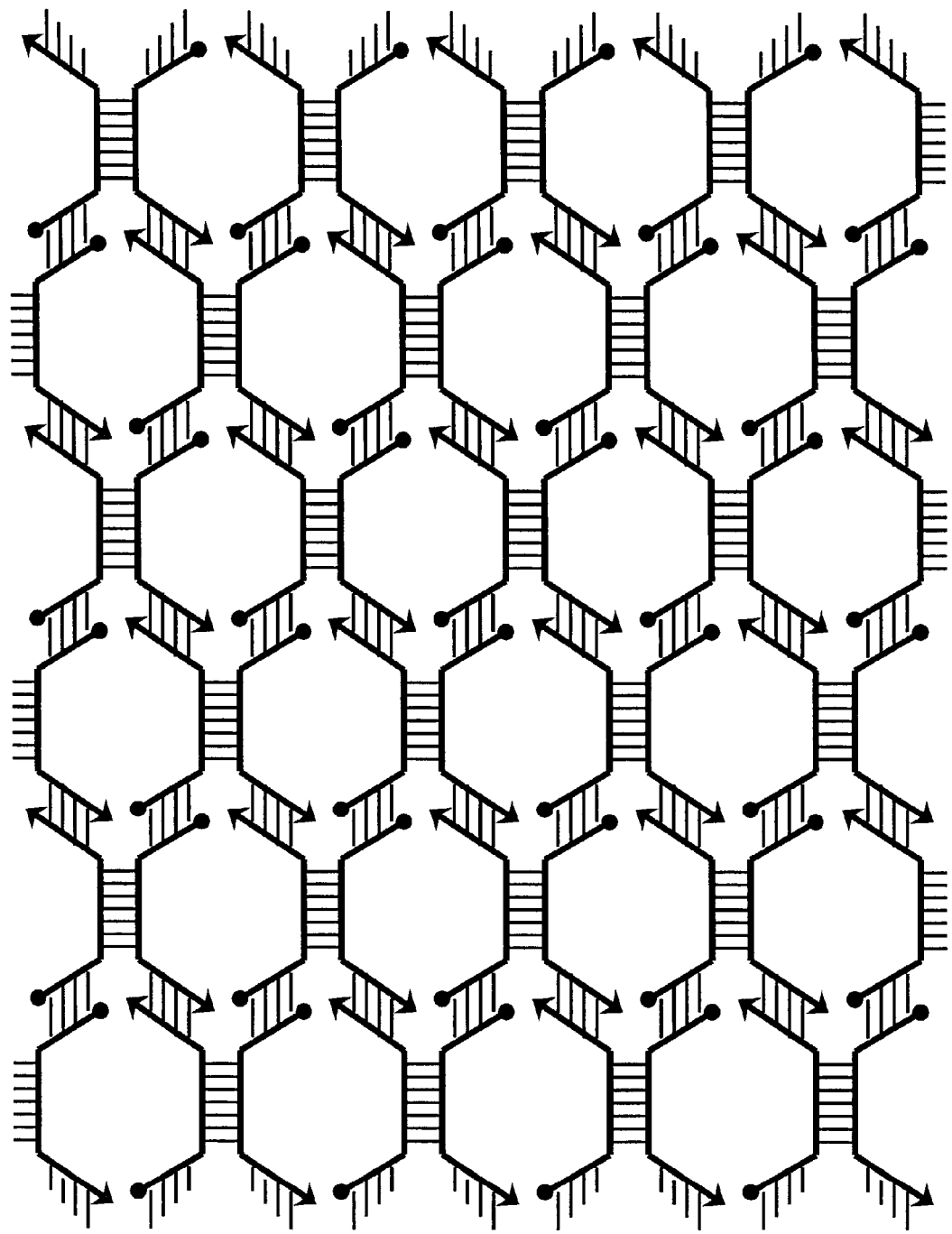
FIG. 4 is a schematic diagram illustrating an example of a three-dimensional conceptual structure of the schematic diagram shown in FIG. 3.
Figure 5:
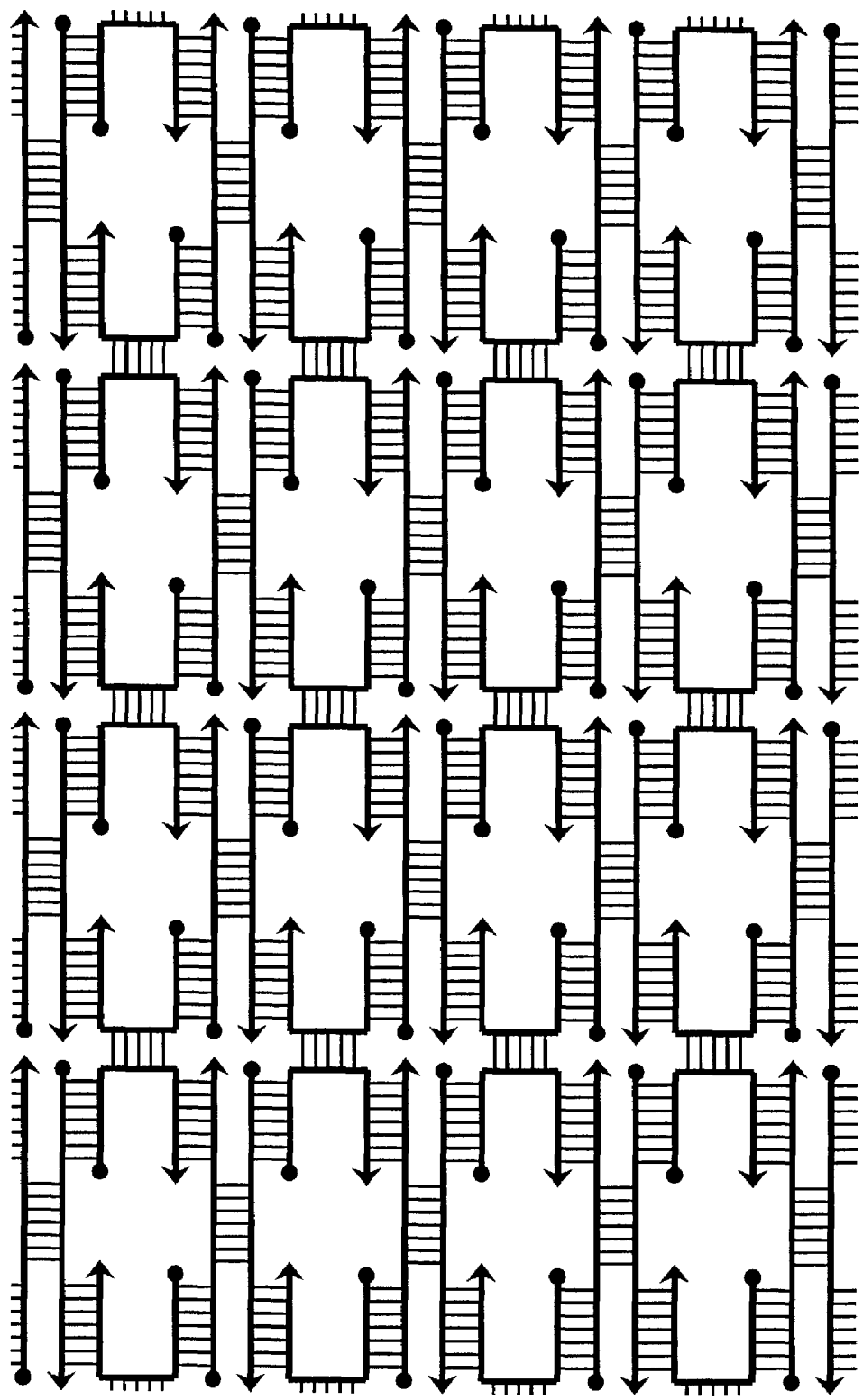
FIG. 5 is a schematic diagram illustrating a pair of DNA probes which hybridize in binding patterns different from those of FIG. 3.
Figure 6:
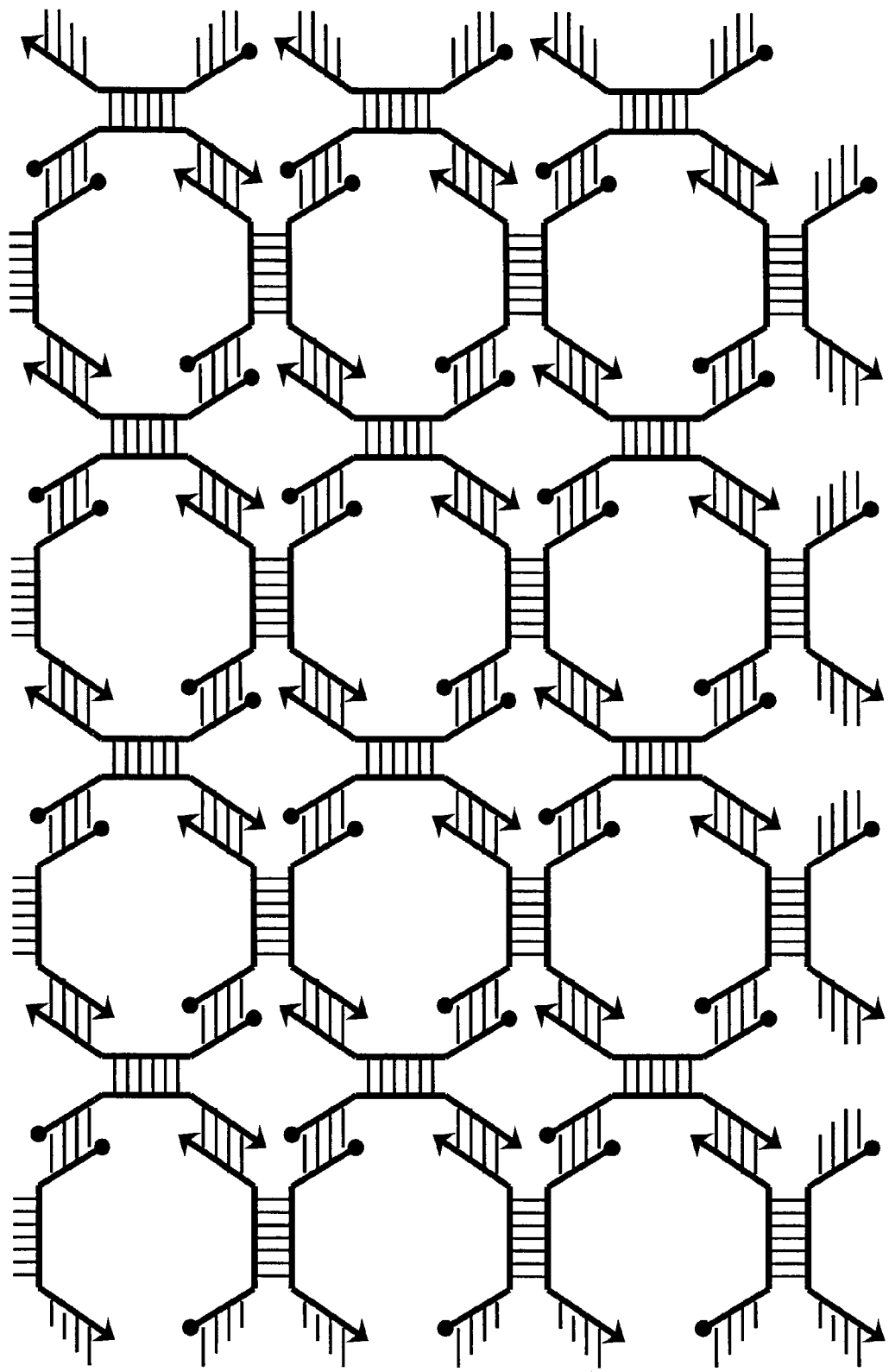
FIG. 6 illustrates an example of a three-dimensional conceptual structure of the schematic diagram of FIG. 5.
Figure 8:
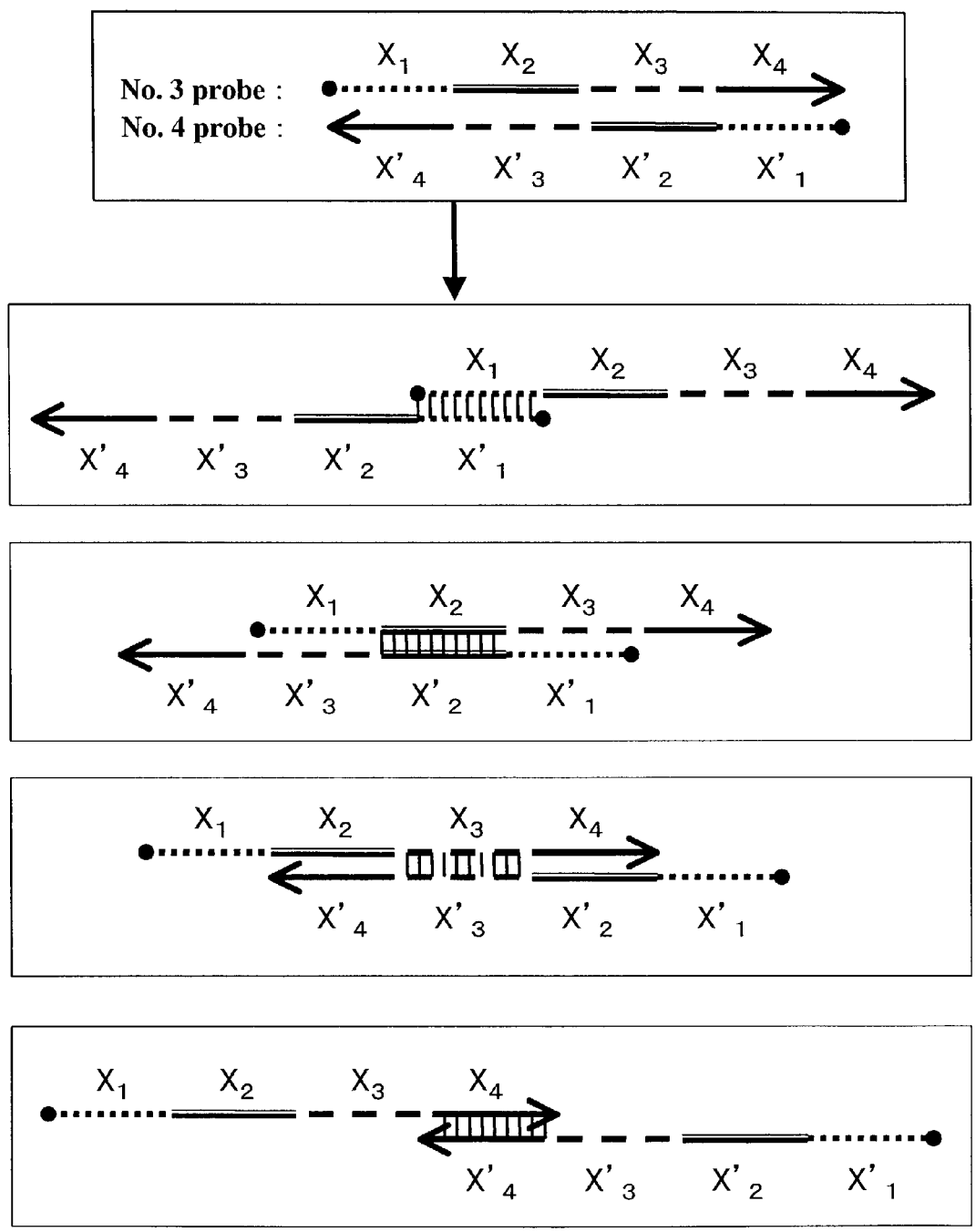
FIG. 8 is a schematic diagram of an example showing how a pair of DNA probes shown in FIG. 7 are bound.
Figure 9:
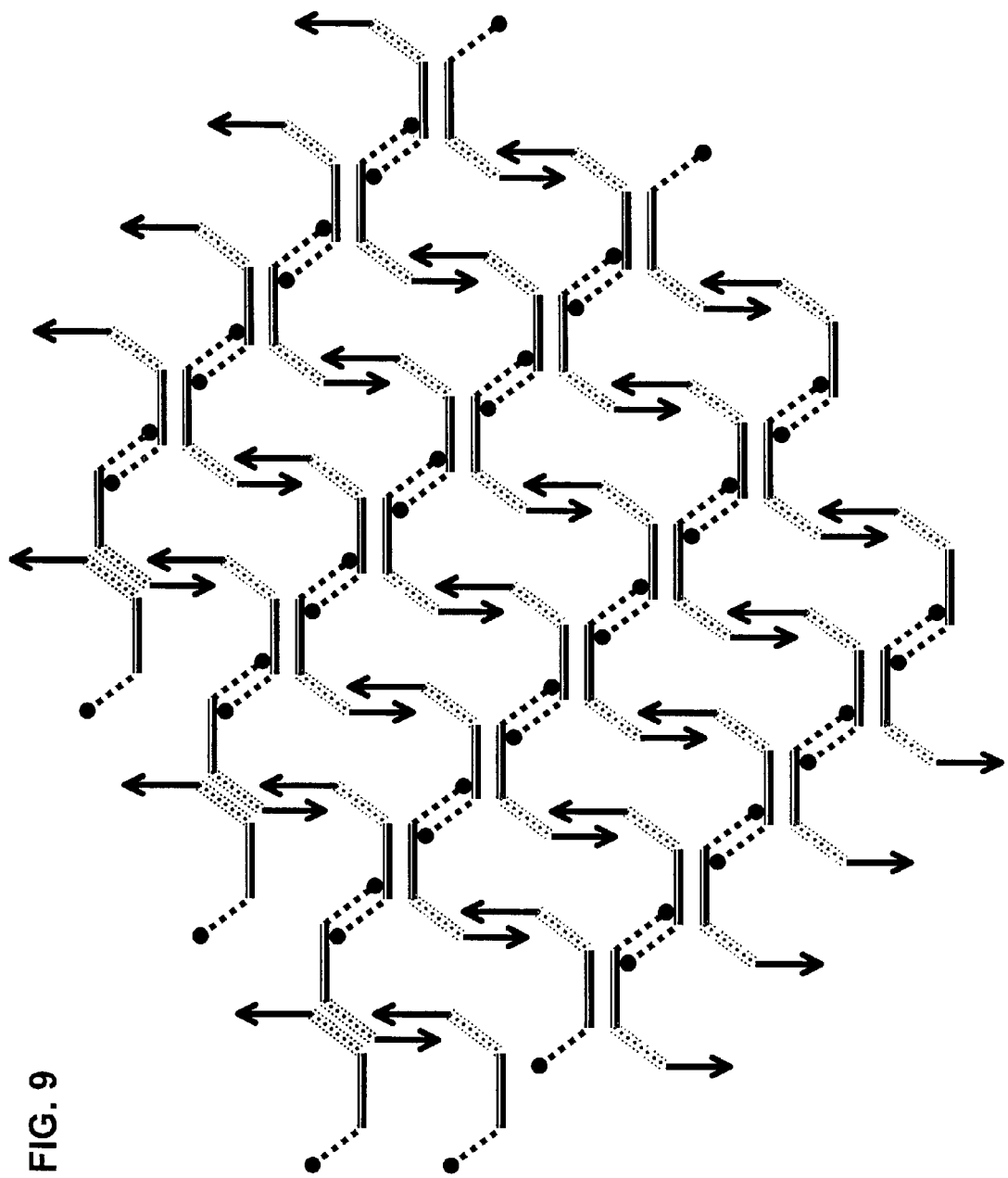
FIG. 9 is a schematic diagram of an example showing the formation of a polymer where a pair of DNA probes hybridize alternately when n is 4.
Figure 11:
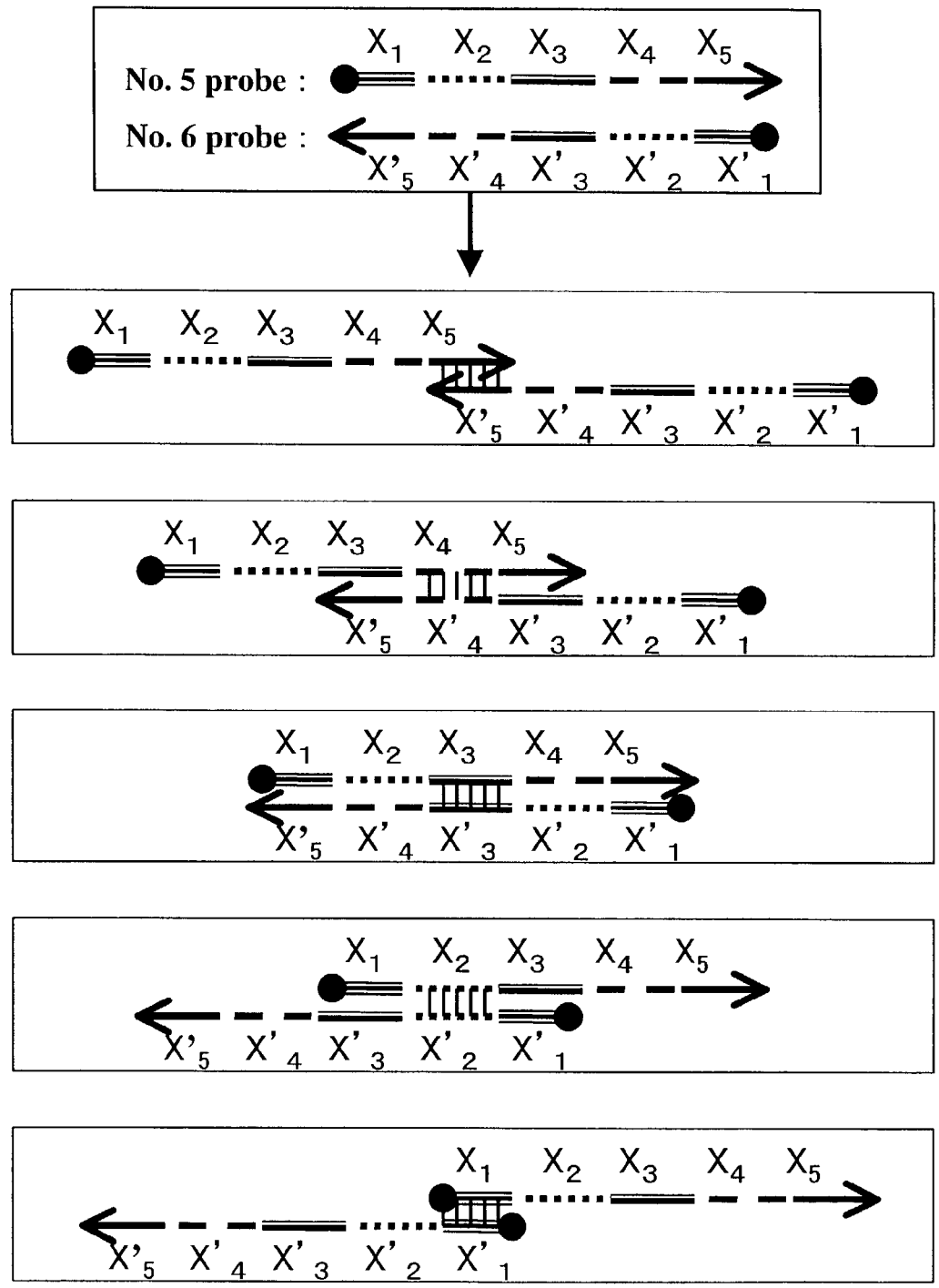
FIG. 11 is a schematic diagram showing how a pair of DNA probes shown in FIG. 10 are bound.
Figure 12:
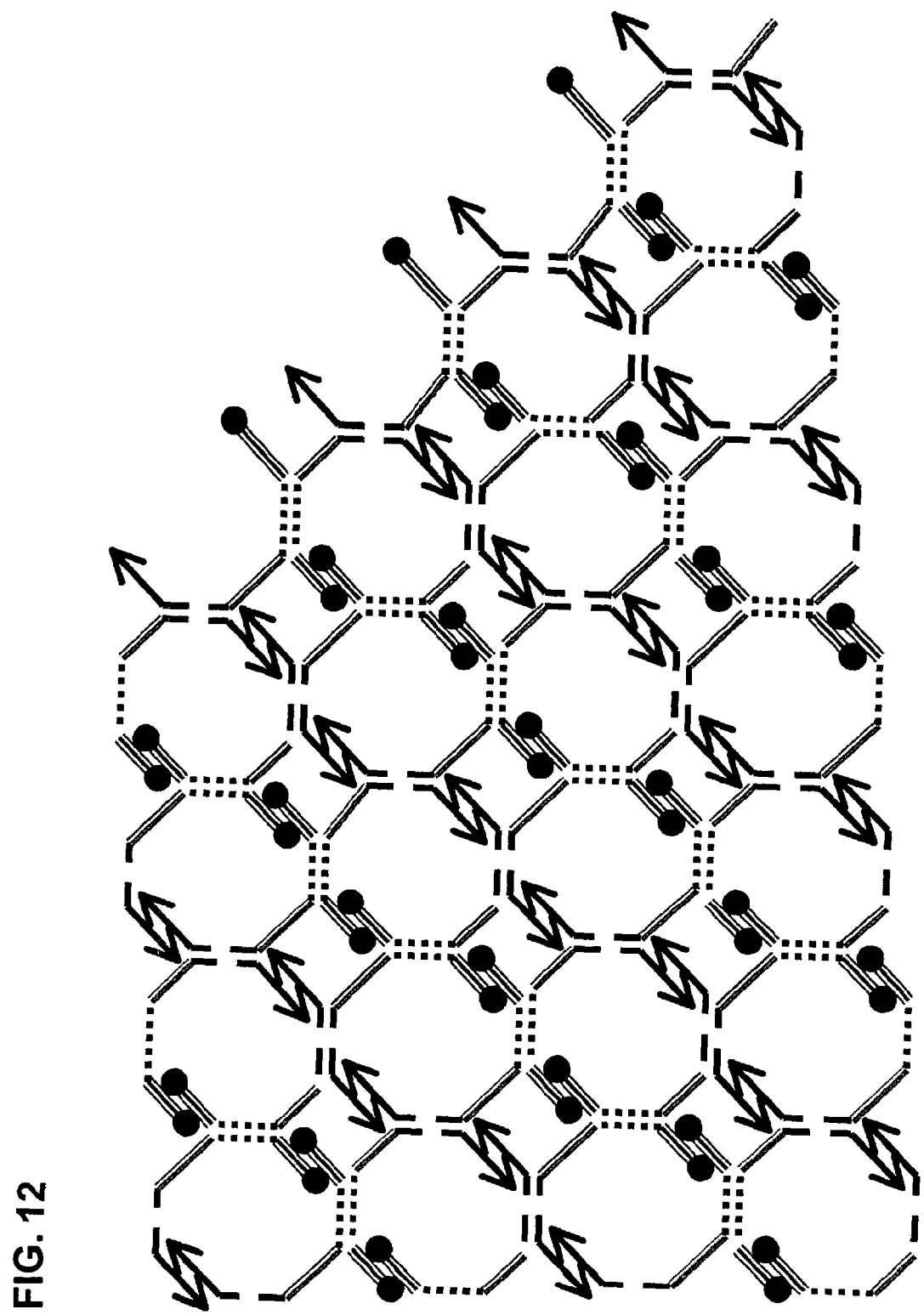
FIG. 12 is a schematic diagram of an example showing the formation of a polymer where a pair of DNA probes hybridize alternately when n is 5.
Figure 13:
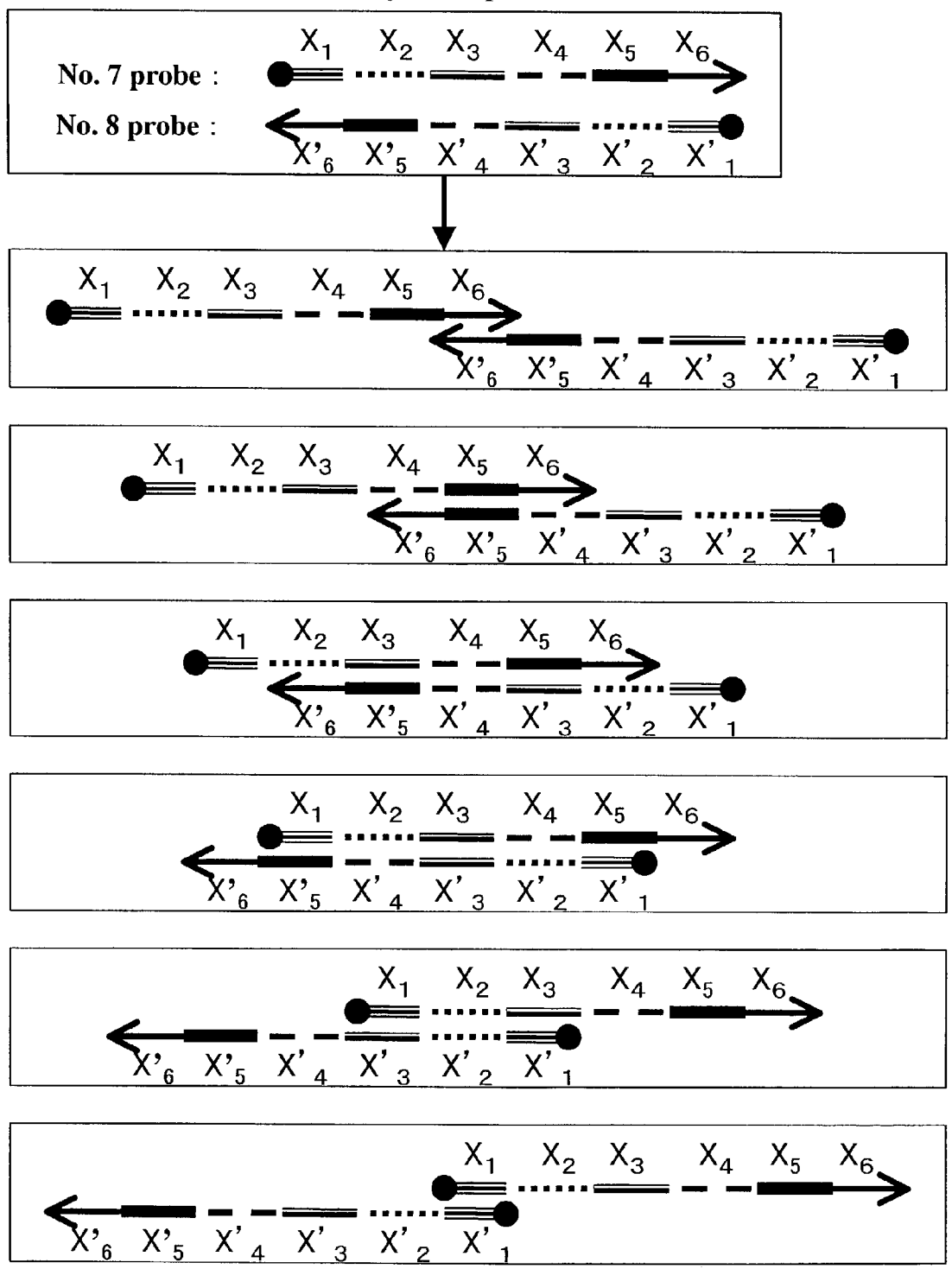
FIG. 13 is a schematic diagram showing how a pair of DNA probes are bound when n is 6.
Figure 14:
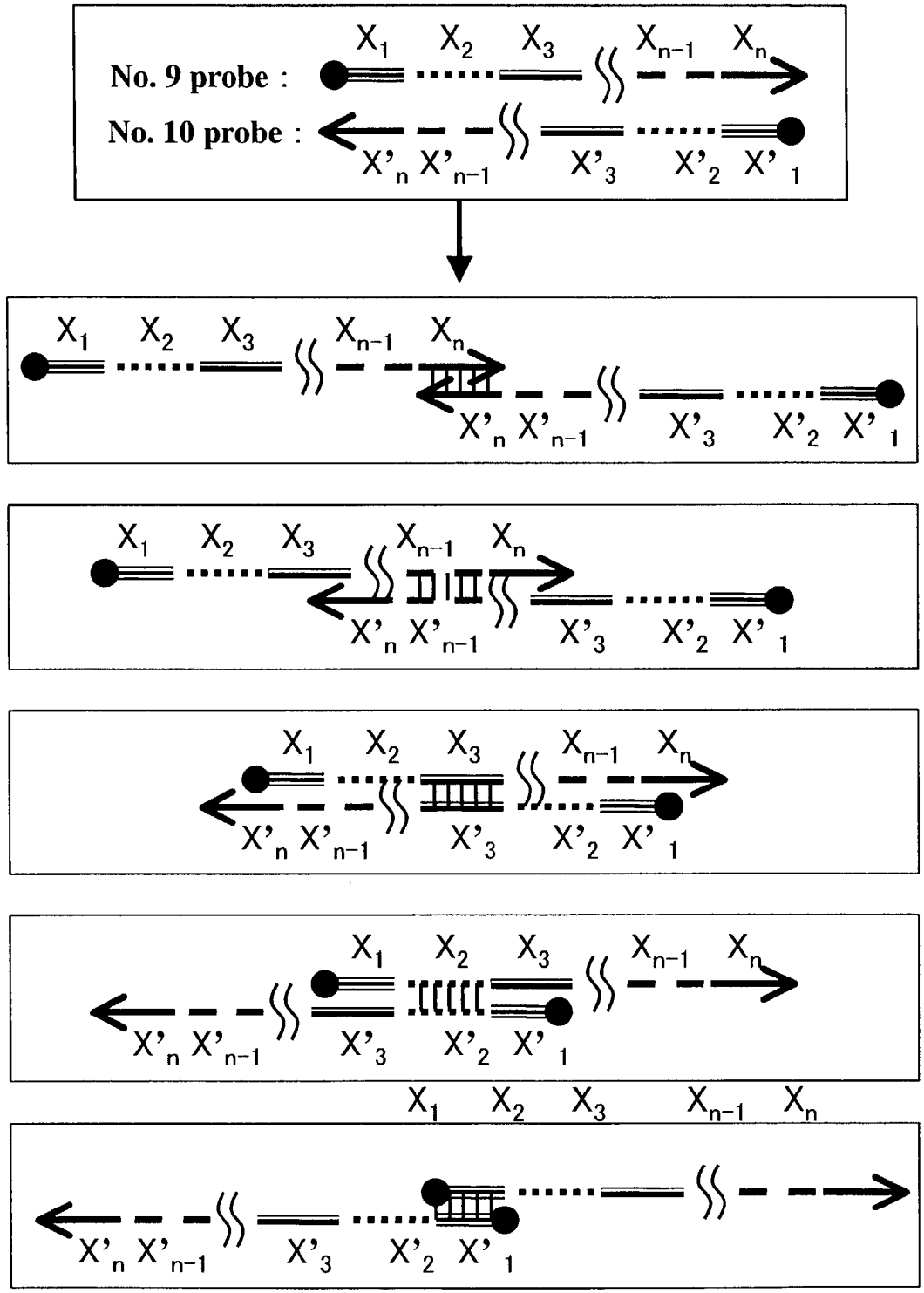
FIG. 14 is a schematic diagram showing how a pair of DNA probes are bound where the number of complementary portions is n.
Figure 18:
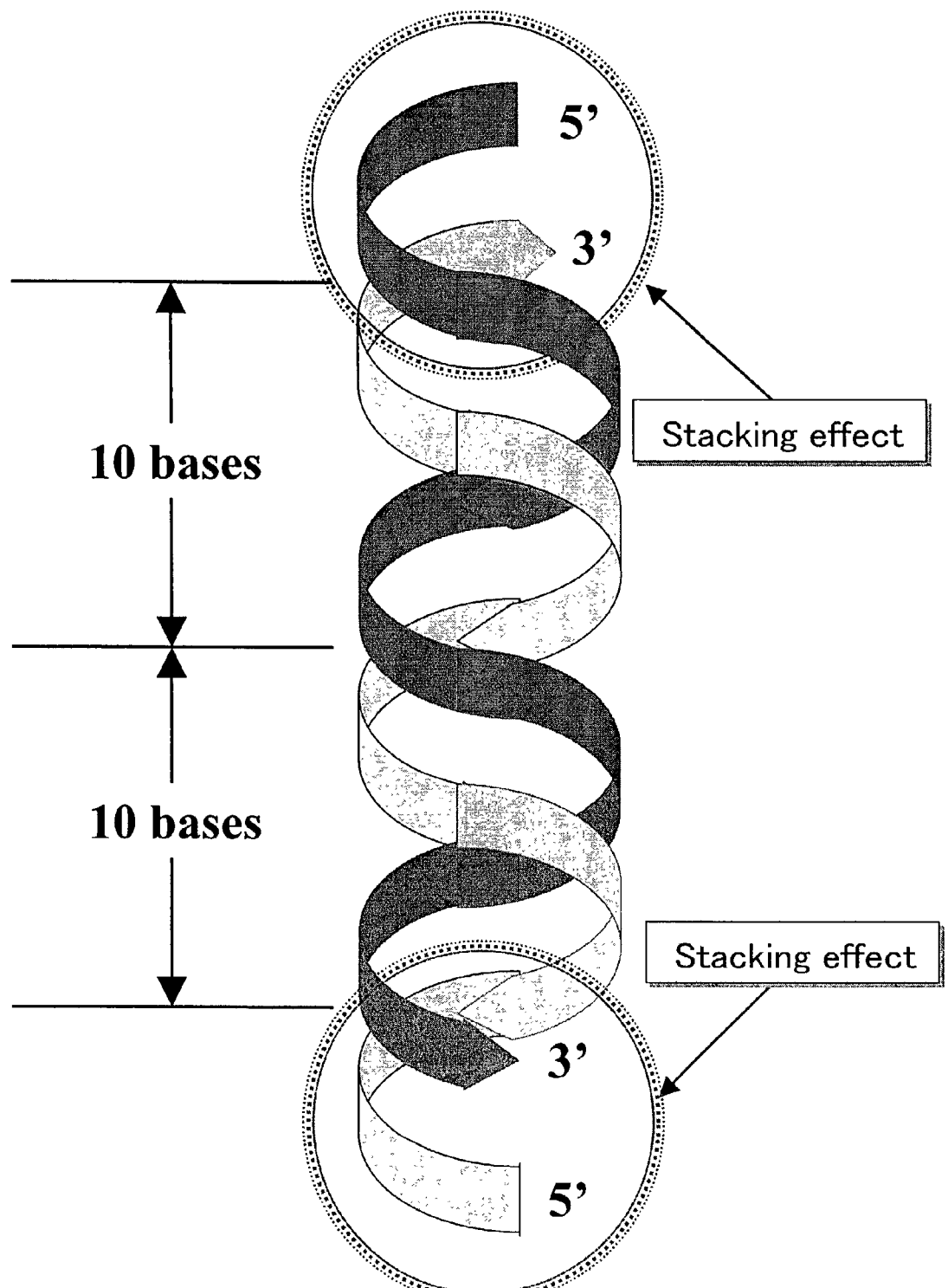
FIG. 18 is a schematic diagram showing the principle of stabilization of hybridization by the stacking effect.
Figure 19:
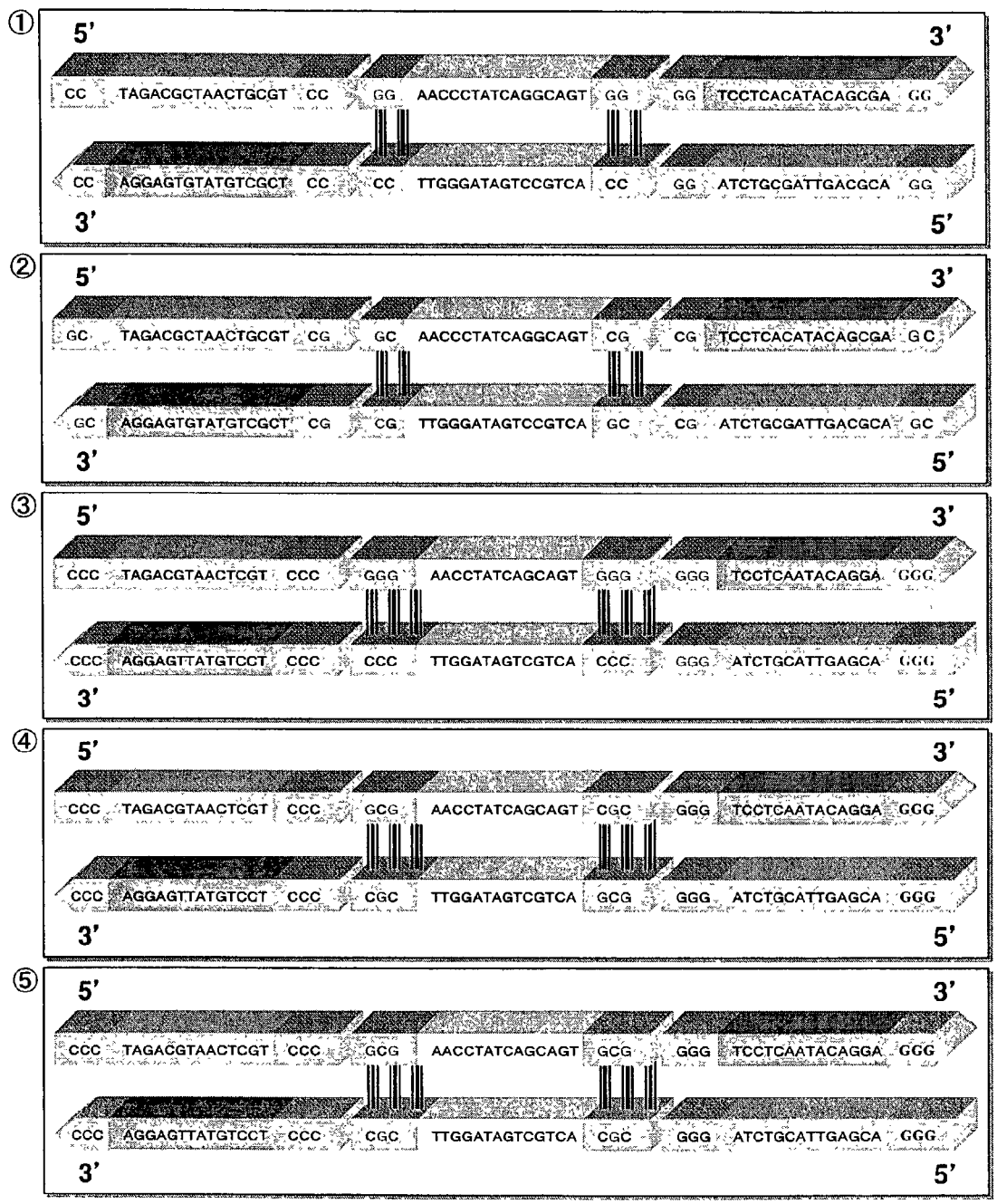
FIG. 19 is a schematic diagram showing synthesis of HCP (where at least one base was replaced) by the use of the stacking effect.

Illustrating the constitution of the present invention using a more specific example, the hybridization of two DNA probes as shown in ① in FIG. 19 may be performed such that when a probe No. 13 and a probe No. 14 are hybridized, sites cleaved by a restriction enzyme are formed (underlined portions are cleaved by a enzyme called "Hae III"), as shown in FIG. 22.

Figure 23:
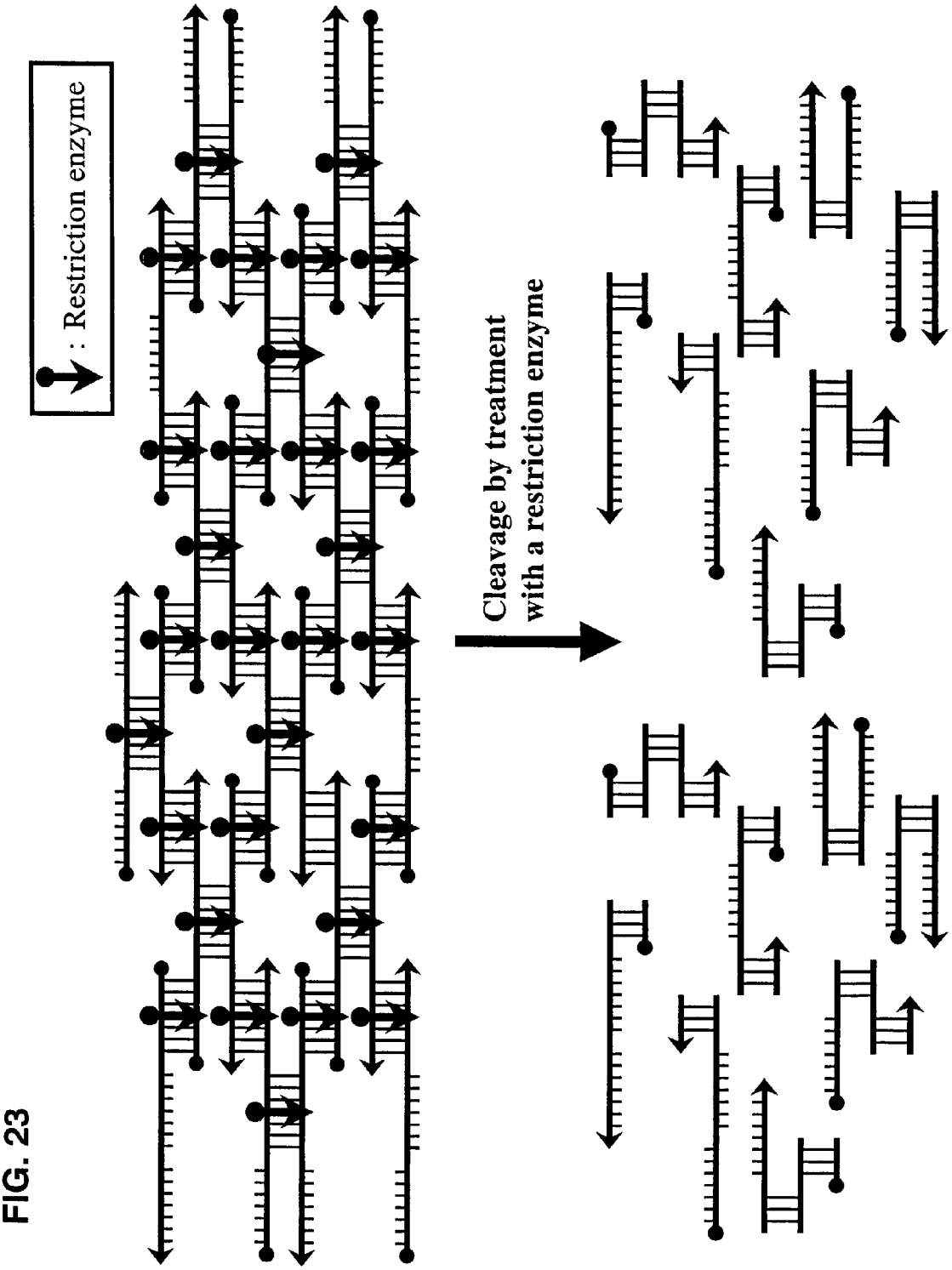
FIG. 23 is a schematic diagram illustrating an example in which probes are three-dimensionally bound alternately to form a polymer which is subsequently cleaved with a restriction enzyme.

In other words, after the probes have alternatively bound in three-dimension to form a polymer, a restriction enzyme can be used to prevent the polymer from cross-contamination in a subsequent different experimental operation (FIG. 23).

In the method of the present invention, base sequences at the branched sites circled in FIG. 17 are designed to form G (guanine)—C (cytosine) bonds upon alternate hybridization, thus the special interaction by π electrons of bases attributable to the staking of bases being generated to form a stable double-stranded polymer. By way of example, FIG. 17 illustrates a pair of probes each composed of three complementary base sequence regions which are hybridized alternately such that the $X_1$ region hybridizes to the $X'_1$ region, the $X_2$ region hybridizes to the $X'_2$ region, and the $X_3$ region hybridizes to the $X'_3$ region.

Figure 40:
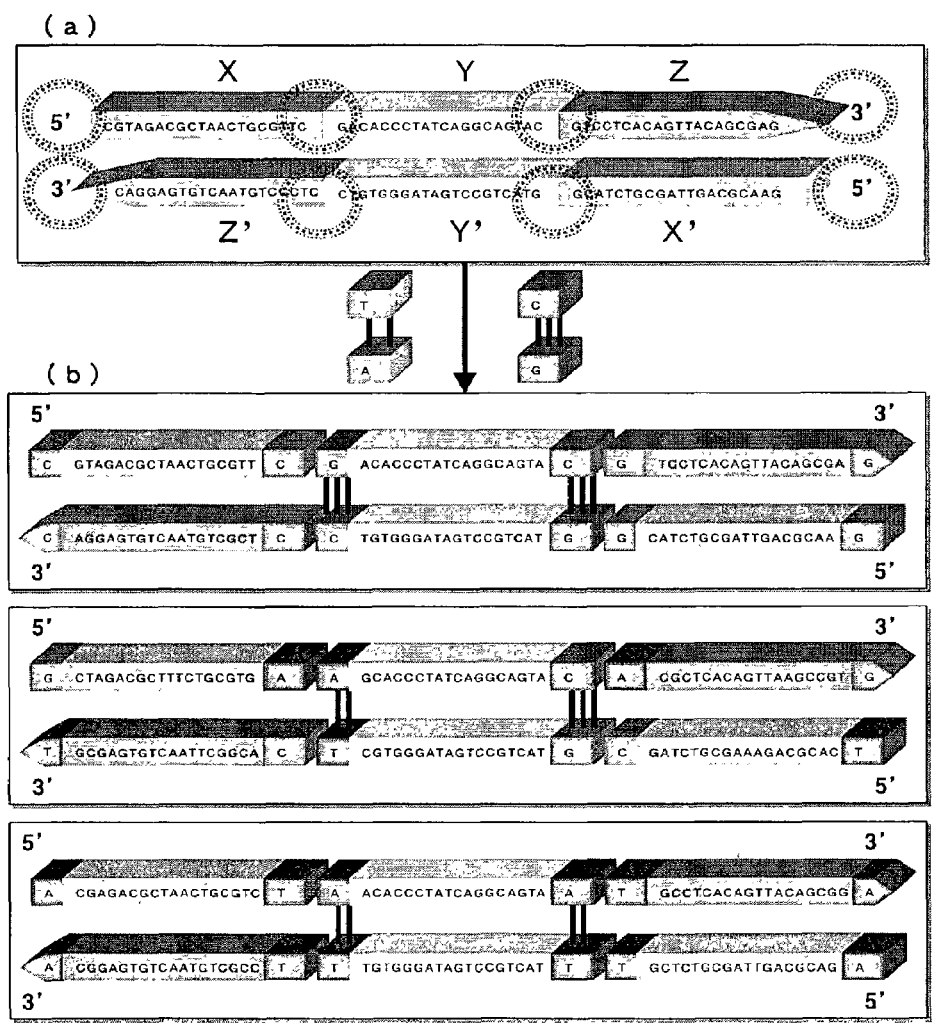
FIG. 40 is a schematic diagram showing the synthesis of HCP (where one base was replaced) by the use of the stacking effect.

FIG. 40(a) shows a probe-polymer which is used in a method (the PALSAR method) for forming a double-stranded probe-polymer and use thereof wherein a plurality of pairs of probes (HCP) each composed of "$n(n \geq 3)$" portions complimentary to each other are hybridized alternately in a crossing state to form a double-stranded polymer.

That is, as shown in FIG. 40(b), bases at branched sites are designed to form G—C bonds, thereby stabilizing the formation of a polymer. Further, the type and number of G—C bonds at each branched site are constituted arbitrarily as shown in ① to ⑤ in FIG. 19, and are not particularly limited insofar as there occur G—C bonds.

Figure 24:
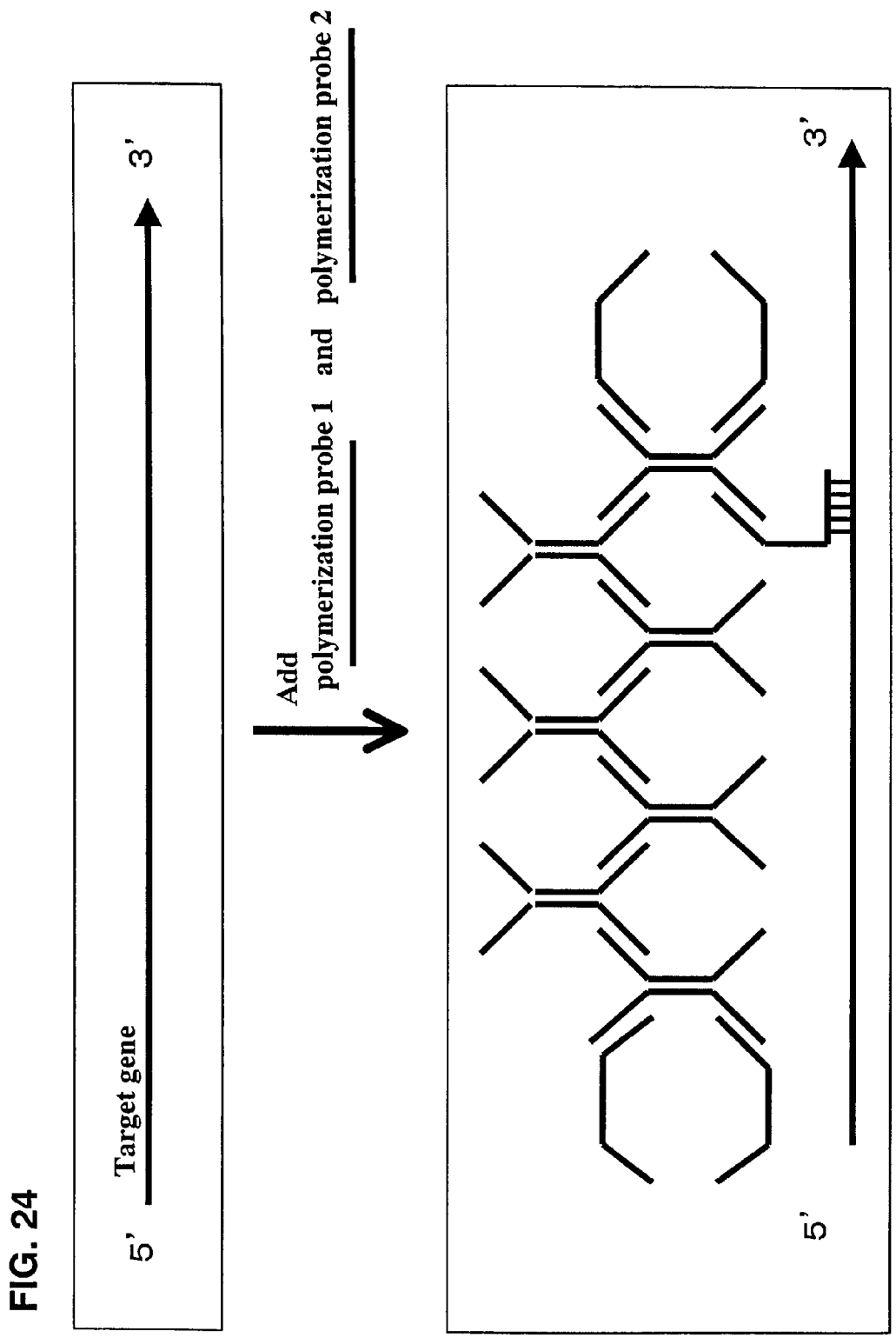
FIG. 24 is a schematic diagram showing a method for directly detecting a target gene using a pair of DNA probes according to the present invention, wherein a probe having regions complementary to a target gene and the pair of DNA probes according to the present invention (polymerization probes in the figure) is hybridized to the target gene, and then the pair of DNA probes according to the present invention (polymerization probes 1 and 2 in the figure) are added to form a double-stranded polymer in the state where the pair of DNA probes according to the present invention are hybridized to the target gene, so that the target gene can be readily detected.
Figure 25:
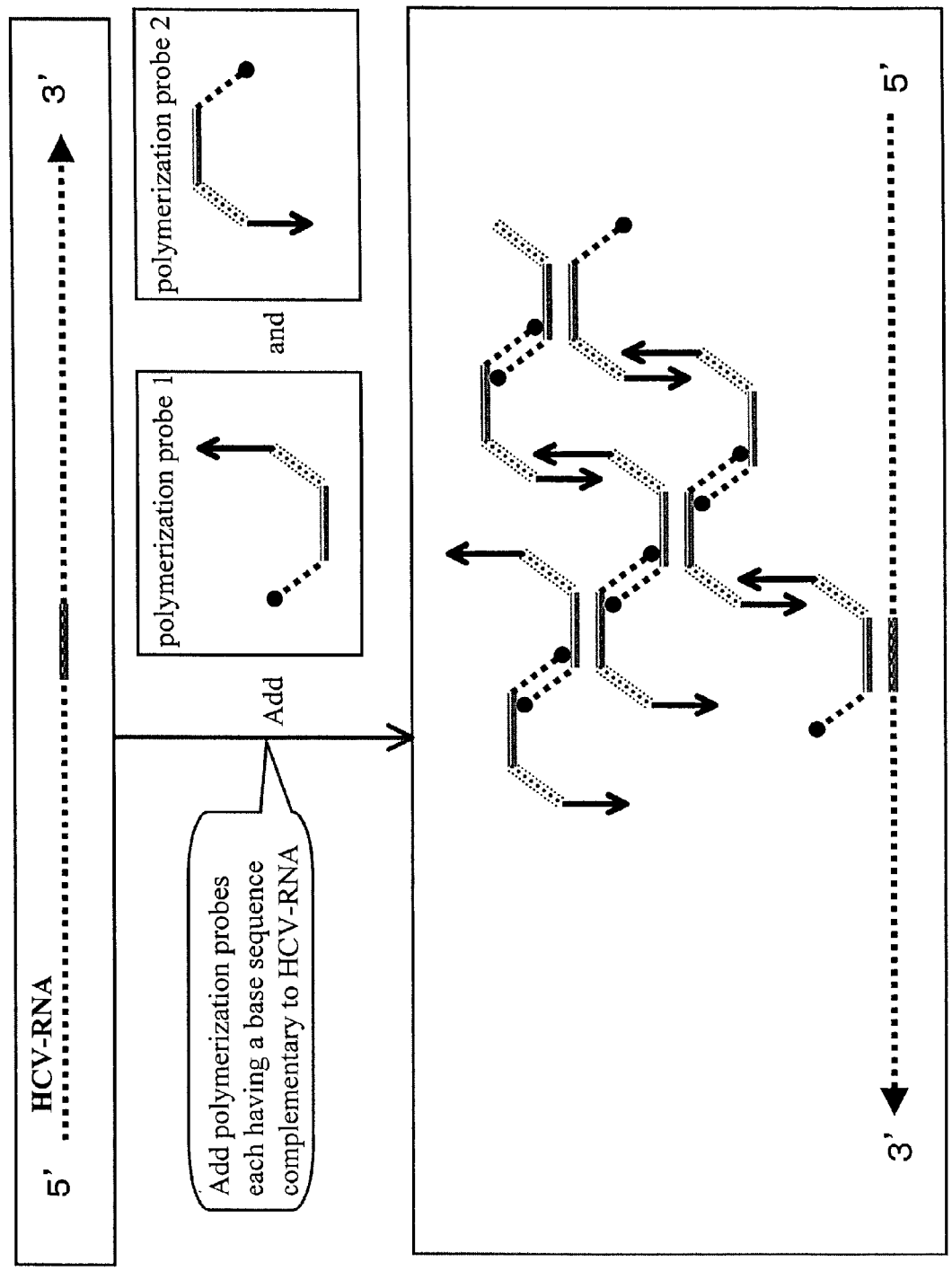
FIG. 25 is a schematic diagram showing a method for detecting a target gene where with a pair of DNA probes wherein n is 4, one of which is a DNA probe (a polymerization probe 1 in the figure) constituted such that a gene in a portion thereof is complementary to a target gene, and the other of which is a DNA probe (a polymerization probe 2 in the figure) making a pair with the above DNA probe, a plurality of the pairs of probes and the target probe are hybridized to form a double-stranded polymer, thereby the target gene being detected.

As shown, for example, in FIGS. 24 and 25, the target gene detecting method according to the present invention comprises, in a first aspect, the steps of: providing a pair of probes, one of which is constituted such that a base sequence of one complementary region in the probe is complementary to a part of a target gene; reacting said probe with the target gene; and then hybridizing a plurality of the pairs of probes to each other to form a target gene-probe-polymer complex. After the complex is separated by suitable techniques, the amount of the probe-polymer can be measured to determine the amount of the target gene.

Figure 26:
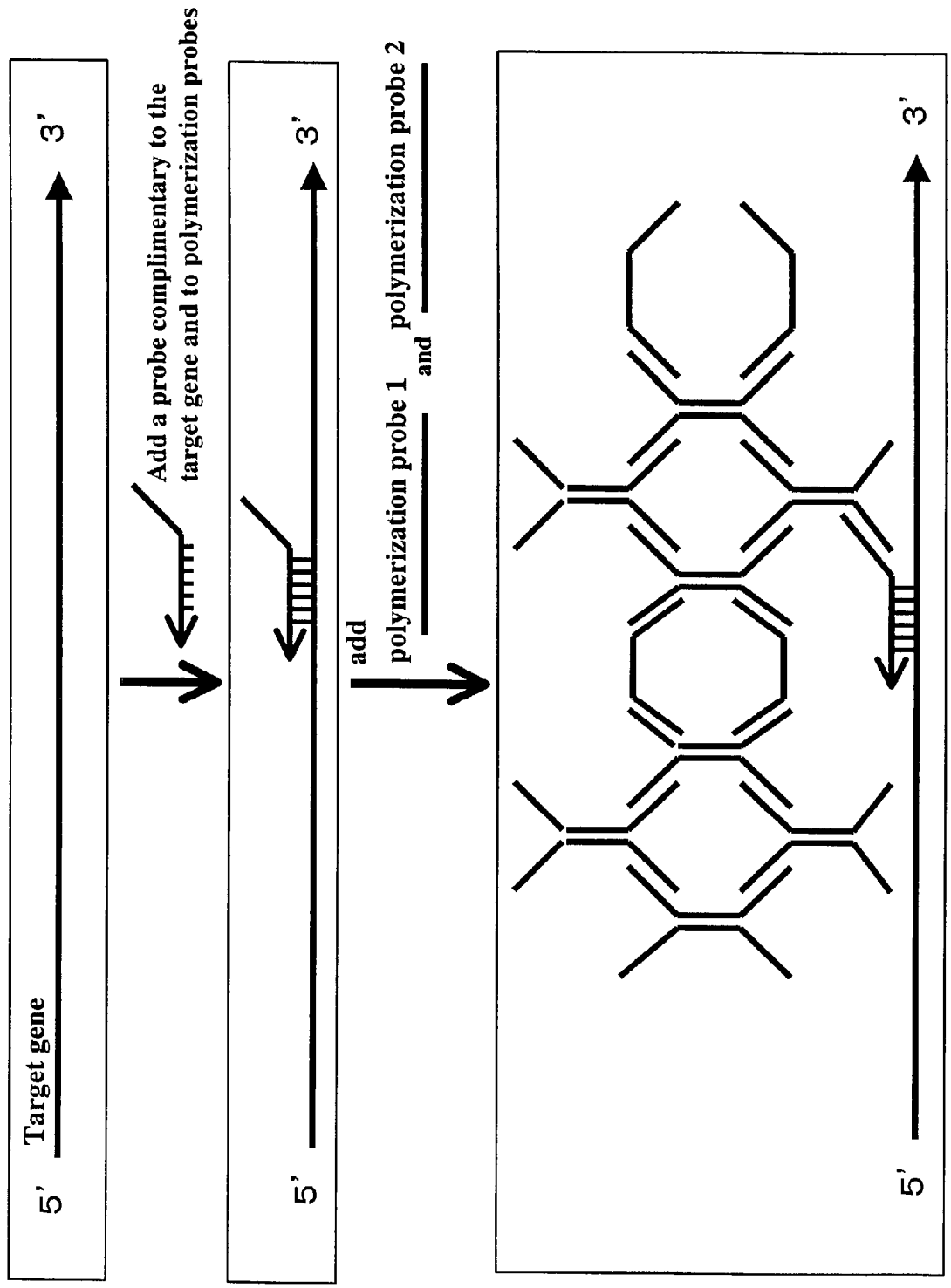
FIG. 26 is a schematic diagram showing a method for detecting a target gene where with a pair of DNA probes, one of which is a DNA probe (a polymerization probe 1 in the figure) constituted such that a gene in a portion thereof is complementary to a target gene, and the other of which is a DNA probe (a polymerization probe 2 in the figure) making a pair with the above DNA probe, a plurality of the pairs of probes and the target probe are hybridized to form a double-stranded polymer, thereby the target gene being detected.

As shown, for example, in FIG. 26, the target gene detecting method according to the present invention comprises, in a second aspect, the steps of: providing a pair of probes and another probe (a capture probe) composed of the same base sequence in a part of either one probe in the pair of probes and a base sequence complementary to a part of a target gene; previously hybridizing the capture probe to the target gene; and hybridizing a plurality of the pairs of probes thereto by the above-described probe-polymerizing method to form a double-stranded polymer, which is detected by amplifying the probes.

The capture probe used in detection of the target gene is composed of at least two regions, that is, a region having a base sequence complementary to a part of the target gene and a region having a base sequence complementary to a region of the polymerization probe, but, e.g., other complementary base sequence regions in the polymerization probe may be arbitrarily added thereto. However, the function of the capture probe should not be deteriorated by such addition. To detect the target gene, at least one capture probe shall be used and if necessary plural kinds of capture probes can also be used by selecting a plurality of base sequences each complementary to a part of the target gene.

In the above target gene-detecting method, the formed probe-polymer can be measured by the following methods. For example, intercalating dyes such as ethidium bromide, Oligreen, SYBR Green I or the like may be bound to the obtained probe-polymer to detect an amplified polymer through fluorescence.

As labeled materials for detection, radioisotope such as $^{125}I$, $^{32}P$ or the like, luminescent and coloring substances such as digoxigenin, acridinium ester or the like, biotin for utilizing fluorescent, luminescent and coloring substances or the like bound to avidin, and a donor fluorescent dye and an acceptor fluorescent dye utilizing fluorescent resonance energy transfer (FRET) may be previously added to a pair of polymerization probes to detect the target gene. The labeled material is not particularly limited.

The pair of probes may be two DNA probes, a DNA probe and an RNA probe, two RNA probes, two PNA probes, a PNA probe and a DNA probe, or a PNA probe and an RNA probe.

Further, the bases constituting one probe are not limited to a kind of base such as DNA or RNA, and, for example, a chimera probe consisting of both DNA and PNA can be used in the present invention.

Those kinds of bases complementary to each other between the above-described pair of probes can be arbitrarily selected from C (cytosine), T (thymine), G (guanine), A (adenine), U (uracil) and so on, and are not particularly limited. Further, the lengths of complementary regions in one probe may be the same or different. The number of probes used in hybridization to form a double-stranded polymer is preferably in the range of $10^2$ to $10^{15}$.

The specific procedure of the present invention for detecting a target gene comprises, e.g., first reacting at least one kind of capture probe with a sample to bind the target gene to the capture probe. In this step, at least one kind of biotinized capture probe is used. Out of a pair of polymerization probes, one probe is then added and reacted, and thereafter the other polymerization probe is reacted therewith to form a target gene-probe-polymer complex. Then, avidin-bound magnetic particles (magnetic beads) are reacted and bound to the complex, and by the use of the properties of the beads, the complex is separated from the unreacted materials. Finally, ethidium bromide is reacted therewith and the amount of the probe-polymer is quantified by ultraviolet irradiation, whereby the amount of the target gene in the sample is measured. To facilitate separation of the formed probe-polymer, magnetic beads may also be used.

Another procedure can make use of, e.g., a well on which an oligonucleotide containing a base sequence complementary to a part of a target gene has been solidified. First, a sample is put onto the well so that a target gene in the sample is bound to the solidified oligonucleotide containing a base sequence complementary to a part of the target gene. Then, the polymerization probes are successively added according to the above-described method, whereby a probe-polymer is formed and bound onto the well. Separation thereof from the unreacted materials can be easily effected by washing the well, and finally the amount of the probe-polymer can be measured to measure the target gene.

This procedure can also be applied to DNA chips.

A sample containing a target gene (DNA or RNA) to be measured in the present invention may be any sample which can contain the nucleic acid. The target gene may be prepared or isolated as necessary from the sample, and is not particularly limited. For example, there are illustrated samples derived from the living organisms, such as blood, serum, urine, feces, cerebrospinal fluid, tissue fluid, cell cultures and so on, and samples suspected of containing, or infected with, viruses, bacteria, fungi and so on. Further, nucleic acids such as DNA or RNA in a target gene in a sample amplified by a known method can also be used. When the target gene is double-stranded DNA, it can be used by changing into single-stranded one by a known method.

The present invention also provides a kit for detecting a target gene by the use of the method of the present invention. As one example, this kit comprises at least one target gene capture probe (containing at least one biotinized capture probe), a pair of polymerization probes, avidin-bound magnetic beads, and ethidium bromide as essential elements. If the polymerization probes that contain a base sequence complementary to the target gene are used, the capture probe can be omitted.

In another example, a solid body (e.g., a well) on which an oligonucleotide containing a base sequence complementary to a part of the target gene has been solidified can be used as an essential element. Besides, a reagent for detection of a probe-polymer, a reaction buffer, a diluent fluid, a standard sample, an adsorption inhibitor or the like may be arbitrarily contained without any particular limitation.

Examples of solid carrier materials include glass, plastics (e.g., polystyrene, polyamide, polyethylene, polypropylene, etc.), metals or the like, and the carrier may be in the form of cup, plate or the like without any particular limitation.

EXAMPLES

Hereinafter, the present invention is described in more detail by reference to Examples, which are not intended to limit the present invention.

1. DNA Probes Used in Examples 1 and 2.
   Probe 1:
   5'-TgA CTT ACT TAA CCg gAA ACA T·AAg CAg gAT CCT CTA AgC CTg A·CgA AgT ATT TAA Cgg Tgg TAT g-3' (SEQ. ID NO: 1)
   Probe 2:
   3'-gCT TCA TAA ATT gCC ACC ATA C·TTC gTC CTA ggA gAT TCg gAc T·ACT gAA TgA ATT ggC CU TgT A-5' (SEQ. ID NO: 2)
   Probe 3:
   5'-TgC CgA CCg gCg AgC g·TAg CAT ggC CCT CTA g·CTT ATC ggC CTC gAg A-3' (SEQ. ID NO: 3)
   Probe 4:
   3'-gAA TAg CCg gAg CTC T·ATC gTA CCg ggA gAT C·ACg gCT ggC CgC TCg C-5' (SEQ. ID NO: 4)

2. Synthetic HCV-RNA and a Variety of DNA Probes Used in Examples 3 and 4.
   HCV-RNA which synthesizes a 5'-noncoding region of hepatitis C virus (abbreviated hereinafter to synthetic HCV-RNA)
   HCV-RNA capture probe A:
   5' (phosphorylated)-TAg AgC gTg CAg ATA gTC gAT·CCT CAC Agg (a meaningless base sequence) (a base ggA gTg ATT CAT ggT-3' (SEQ ID. NO: 5) sequence complementary to HCV-RNA)
   HCV-RNA capture probe B:
   5' (biotin-labeled)-TAg AgC gTg CAg ATA gTC gAT·CCT CAC Agg (a meaningless base sequence) (a base ggA gTg ATT CAT ggT-3' (SEQ ID. NO: 6) sequence complementary to HCV-RNA)
   Capture probe C:
   3'-TAC TTA gTg Agg ggA CAC TCC·gAA TAA gTC ATA gCT CAT-5' (SEQ. ID NO: 7) (a base sequence complementary to HCV-RNA) (a base sequence complementary to the probe 5)
   Capture probe D:
   3'-gCC CAg gAA AgA ACC TAg TTg·gAA TAA gTC ATA gCT CAT-5' (SEQ. ID NO: 8) (a base sequence complementary to HCV-RNA) (a base sequence complementary to the probe 5)
   Capture probe E:
   3'-CAT CAC AAC CCA gCg CTT TCC·gAA TAA gTC ATA gCT CAT-5' (SEQ ID NO: 9) (A base sequence complementary to HCV-RNA) (a base sequence complementary to the probe 5)
   Probe 5:
   5'-CTT ATT CAg TAT CgA gTA·TAg CAg gAT CCC TCT Aag·TgC (a base sequence complementary to the capture probes B, C, D) Cgg ACC AgC gAg Cgg-3' (SEQ. ID NO: 10)
   Probe 6:
   3'-ACg gCC Tgg TCg CTC gCC·ATC gTC CTA ggg AgA TTC·gAA TAA gTC ATA gCT CAT-5' (SEQ. ID NO. 11)
   Probe 7:
   3'-(biotinized)-ACg gCC Tgg TCg CTC gCC·ATC gTC CTA ggg AgA TTC·gAA TAA gTC ATA gCT CAT-5' (SEQ ID NO: 12)

Example 1

1. Object
The effect of polymerization with respect to hybridization temperature was proved using polymerization probes which are a pair of DNA probes according to the present invention.

2. Materials
   1) Probes 1 and 2 were used in polymerization.
   2) 20×SSC (3 M-NaCl, 0.3 M-$C_6H_5O_7Na_3 \cdot 2H_2O$, pH 7.0) was used as a buffer solution.

3. Procedure
5 μL of the probes 1 and 2 each prepared to be $10^{13}$ copies/μL were added in 0.2 mL sterilized microtubes respectively, then 40 μL of 20×SSC were further added, and those microtubes were covered with a lid. Then, those microtubes were boiled at 94° C. for 30 seconds and warmed at 50° C., 52° C., 54° C., 56° C., 58° C., 60° C., 64° C., 66° C., 68° C. and 70° C. for 30 minutes, respectively.

After the warming, electrophoresis was performed using 0.5% agarose gel to confirm the effect of the polymerization through ethidium bromide staining.

4. Results
FIG. 27 is a photograph showing the results of Example 1 with electrophoresis at 100 V for 30 minutes using 0.5% agarose gel.

The agarose gel is a gel which can divide DNA molecules according to the size, and 0.5% agarose gel is generally used to separate DNA molecules of 30,000 to 40,000 base pairs.

The photograph of FIG. 27 shows a polymer which has grown so much with increasing temperatures that it can no longer migrate with 0.5% agarose gel as a result of the fact that a double-stranded polymer has been exactly and alternately formed by the pair of DNA probes depending on the temperature of hybridization.

Example 2

1. Object
It was proved that a polymer polymerized by polymerization probes, i.e., a pair of DNA probes according to the present invention can be cleaved by a restriction enzyme.

2. Materials
   1) Probes 3 and 4 were used in polymerization.
   2) Hae III (made by Takara Shuzo Co., Ltd.) was used as a restriction enzyme.
   3) M-Buffer (made by Takara Shuzo Co., Ltd.) was used as a buffer solution for the restriction enzyme.
   4) 20×SSC was used as a buffering solution.

3. Procedure
5 μL of the probes 3 and 4 each prepared to be $10^{13}$ copies/μL were added in a 0.2 mL sterilized microtube respectively, then 5 μL of 20×SSC and 35 μL of sterilized distilled water were further added to produce a reaction solution A, and the microtube was covered with a lid. Similarly to the reaction solution A, 2.5 μL of the probes 3 and 4 each prepared to be $10^{13}$ copies/μL were added in a 0.2 mL sterilized microtube respectively, then 5 μL of 20×SSC and 40 μL of sterilized distilled water were further added to produce a reaction solution B, and the microtube was covered with a lid. The reaction solutions A and B were boiled at 94° C. for 30 seconds and warmed at 62° C. for 30 minutes, respectively.

After the warming, 5 μL of M-buffer and 5 μL of Hae III were added to each of 40 μL of the reaction solutions A and B for reaction at 37° C. for 24 hours, and electrophoresis was performed using 2% agarose gel to confirm the cleavage of a polymerized polymer by the restriction enzyme through ethidium bromide staining.

4. Results

Figure 28:
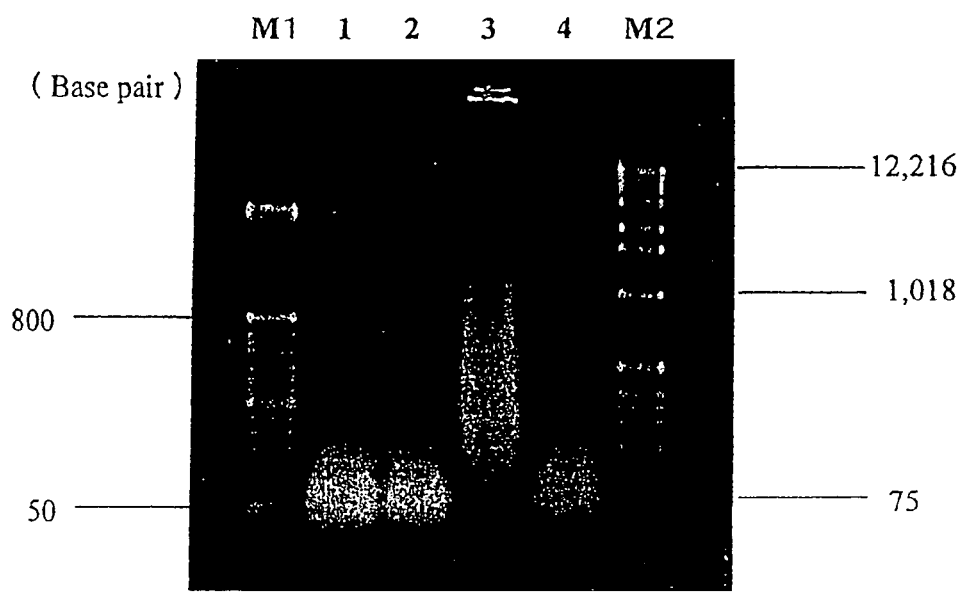
FIG. 28 is a photograph showing the results of Example 2.

FIG. 28 is a photograph showing the results of Example 2 with electrophoresis at 100 V for 30 minutes using 2.0% agarose gel.

The photograph shows that a pair of DNA probes forming exactly and alternately a double-stranded polymer was cleaved to minimum units by the restriction enzyme.

Example 3

1. Materials

1) Probes 5 and 6 were used in polymerization.

2) Magnetic beads bound with streptavidin (product name: Streptavidin MagneSphere made by Promega, Inc.) was used for a solid phase for B/F separation.

3) 20×SSC and 0.5×SSC (40-times diluent of 20×SSC) were used as buffer solutions.

2. Procedure

10 µL each of synthetic HCV-RNA prepared to be $10^1$ copies/10 µL, $10^2$ copies/10 µL, $10^3$ copies/10 µL, $10^4$ copies/10 µL, $10^5$ copies/10 µL, $10^6$ copies/10 µL, $10^7$ copies/10 µL, $10^8$ copies/10 µL, $10^9$ copies/10 µL, and $10^{10}$ copies/10 µL were added in a 0.2 mL sterilized microtube, respectively. Then, 1 µL each of the HCV-RNA capture probe B, probe C, probe D and probe E prepared to be $10^{13}$ copies/µL, 10 µL of the probe 5 prepared to be $10^{13}$ copies/µL, and 25 µL of 20×SSC were added, respectively. The respective microtubes were covered with a lid, and the ingredients were mixed by a mixer and warmed at 62° C. for 60 minutes.

Once the temperature lowered to room temperature, 5 µL of the probe 6 prepared to be $10^{13}$ copies/µL were added to each of those microtube. Then, each of those microtubes was covered with a lid, and the ingredients were mixed by a mixer and warmed at 62° C. for 60 minutes.

Once the temperature lowered to room temperature, 10 µL of Streptavidin MagneSphere (hereinafter referred to as the "magnetic beads") were added to each of the microtubes for reaction at 37° C. for 30 minutes. After the reaction, the magnetic beads were trapped using a magnet, and the supernatant was removed. Then, 50 µL of 0.5×SSC and 10 µL of ethidium bromide (made by Wako Junyaku Co., Ltd.) prepared to be 100 µg/mL were added for reaction at room temperature for 20 minutes.

After the reaction, the magnetic beads were trapped using a magnet, and the supernatant was removed. Then, 50 µL of 0.5×SSC were added. Immediately thereafter, the magnetic beads were trapped using a magnet and the supernatant was removed. Then, 50 µL of 0.5×SSC were added, and all ingredients were transferred to a flat-bottom 96-well plate. Ultraviolet rays were irradiated from the bottom of the 96-well plate, and a probe-polymer which ended up to emit fluorescence by intercalation of ethidium bromide was photographed.

3. Results

Figure 29:
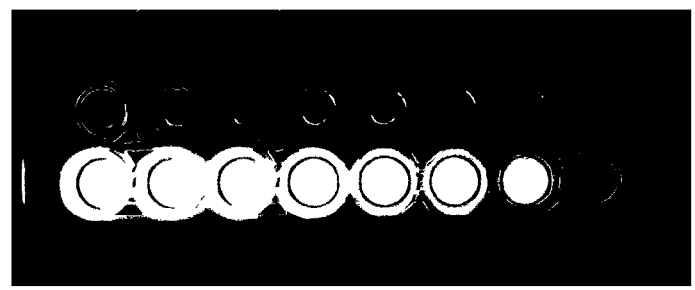
FIG. 29 is a photograph showing the results of Example 3.

FIG. 29 is a photograph showing the fluorescence by the ethidium bromide produced by irradiating ultraviolet rays from the bottom of the 96-well plate.

As can be seen in FIG. 29, the strongest fluorescence was found at $10^{10}$ copies/10 µL, and the fluorescence became gradually weaker in accordance with the amount of synthetic HCV-RNA.

Example 4

1. Materials

1) Probes 5 and 7 were used in polymerization.

2) A 96-well plate (product name: NucleoLink™ made by Nunc, Inc.) was used for a solid phase for B/F separation.

3) "HPR-Streptavidin" made by ZYMED Laboratories, Inc. was used as Peroxidase Conjugated Streptavidin.

4) "A coloring kit T for peroxidase" made by Sumitomo Bakelite Co., Ltd. was used as a coloring reagent.

5) 2N $H_2SO_4$ was used as an enzyme reaction stop solution.

6) 20×SSC and 0.5×SSC were used as buffer solutions.

2. Procedure

10 µL each of synthetic HCV-RNA prepared to be 0 copy/10 µL, $10^3$ copies/10 µL, $10^4$ copies/10 µL, $10^5$ copies/10 µL, $10^6$ copies/10 µL and $10^7$ copies/10 µL were added to each of wells in a 96-well plate (NucleoLink™ made by Nunc, Inc.) previously bound with the HCV-RNA capture probe A (special blocking was not applied). Then, 10 µL each of the capture probe C, the capture probe D and the capture probe E prepared to be $10^{11}$ copies/µL, 10 µL of the probe 5 prepared to be $10^{11}$ copies/µL, and 60 µL of 20×SSC were added, respectively.

After mixing the ingredients by a pipette, they were heated at 94° C. for 30 seconds and warmed at 62° C. for 60 minutes.

Once the temperature lowered to room temperature, 10 µL of the probe 5 prepared to be $10^{11}$ copies/µL and 20 µL of the probe 7 were added to each of those microtubes. They were mixed by a pipette, then heated at 94° C. for 30 seconds and warmed at 62° C. for 60 minutes.

After the temperature lowered to room temperature, each well was washed 4 times with 0.5×SSC containing 0.1% Tween 20. 100 µL of "HRP-Streptavidin" were added to each well and warmed at 37° C. for 20 minutes. After removing the solution in each well by means of suction, each well was washed 4 times with 0.5×SSC containing 0.1% Tween 20. 100 µL of the coloring kit T for peroxidase were added to each well for reaction in a dark room (at room temperature) for 10 minutes. After the reaction, 100 µL of the enzyme reaction stop solution were added, and the absorbance was measured at a wavelength of 450 nm.

3. Results

The results of Example 4 are shown in Table 1.

Color development was confirmed in accordance with the amount of added synthesized HCV-RNA in the range of $10^3$ to $10^7$ copies from the fact that color development was observed in Peroxidase Conjugated Streptavidin labeled at one of a pair of DNA probes which were hybridized alternately to form a double-stranded polymer.

TABLE 1

| Number of copies | Absorbance |
| --- | --- |
| 0 | 1.497 |
| $10^3$ | 1.843 |
| $10^4$ | 1.897 |
| $10^5$ | 1.955 |
| $10^6$ | 2.064 |
| $10^7$ | 2.343 |

Example 5

1. Object

The effect of polymerization with respect to hybridization temperature was proved using a pair of DNA probes each composed of four portions complementary to each other according to the present invention.

2. Materials

In polymerization, the following probes 8 and 9 were used:

Probe 8:
5'-CGGGTCCTTTCTTGG-CATCACAACCCAGCG -TTCCTGACCAGCGAG-TAGCAGGATCCC TCT-3' (SEQ ID NO:13)

Probe 9:
5'-CCAAGAAAGGACCCG-CGCTGGGTTGTGATG- CTCGCTGGTCAGGAA -AGAGGGATCCTGCTA-3' (SEQ. ID NO: 14)

20×SSC was used as a buffer solution.

3. Procedure

5 µL each of the probes 8 and 9 prepared to be $10^{13}$ copies/µL were added to 0.2 mL sterilized microtubes, then 40 µL of 20×SSC were added, each of those microtubes was covered with a lid, and the ingredients were warmed at 54° C., 56° C., 58° C., 60° C., 62° C., 64° C., 66° C. and 70° C. respectively for 30 minutes.

After the warming, electrophoresis was performed using 0.5% agarose gel, and the effect of temperature on polymerization was confirmed by ethidium bromide staining.

4. Results

Figure 30:
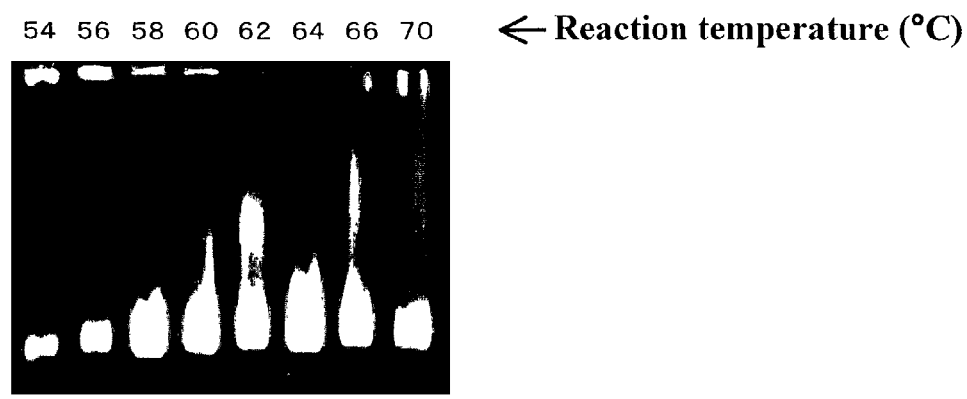
FIG. 30 is a photograph showing the results of Example 5.

FIG. 30 shows the results of Example 5 by electrophoresis at 100 V for 30 minutes using 0.5% agarose gel. A double-stranded polymer formed depending on the respective temperatures was confirmed.

Example 6

1. Object

The effect of polymerization with respect to hybridization temperature was proved using a pair of DNA probes each composed of five portions complementary to each other according to the present invention.

2. Materials

Probes 10 and 11 were used in polymerization.

Probe 10:
5'-CGGGTCCTTTCTTGG-CATCACAACCCAGCG- TTCCTGACCAGCGAG -TAGCAGGATCCCTCT- CTTATTCAGTATCGA-3' (SEQ. ID NO: 15)

Probe 11:
5'-CCAAGAAAGGACCCG-CGCTGGGTTGTGATG- CTCGCTGGTCAGGAA -AGAGGGATCCTGCTA- TCGATACTGAATAAG-3' (SEQ. ID NO: 16)

20×SSC was used as a buffer solution.

3. Procedure

5 µL each of the probes 10 and 11 prepared to be $10^{13}$ copies/µL were added to 0.2 mL sterilized microtubes, then 40 µL of 20×SSC were added thereto, each of those microtubes was covered with a lid, and the ingredients were warmed at 54° C., 56° C., 58° C., 60° C., 62° C., 64° C., 66° C. and 70° C. respectively for 30 minute. After the warming, electrophoresis was performed using 0.5% agarose gel, and the effect of polymerization was confirmed by ethidium bromide staining.

4. Results

Figure 31:
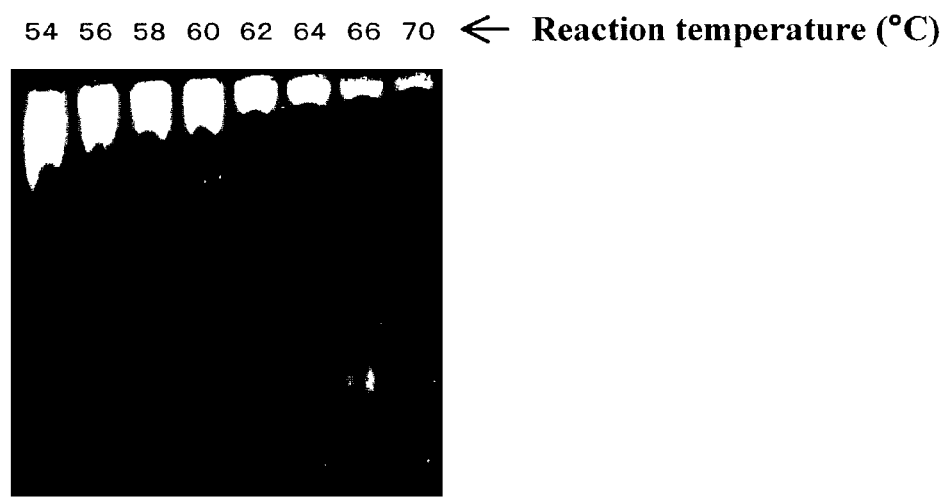
FIG. 31 is a photograph showing the results of Example 6.

FIG. 31 shows the results of Example 6 by electrophoresis at 100 V for 30 minutes using 0.5% agarose gel. A double-stranded polymer formed depending on the respective temperatures was confirmed.

Synthesis Example 1

Oligonucleotide probes having the base sequences shown in FIG. 32 were synthesized by a usual method.

These pairs of synthesized oligonucleotide probes each composed of three regions complementary to each other, were designed from top to bottom in FIG. 32 to have both G—C bonds, one G—C bond, and both A—T bonds as a base pair at two branched sites in each region, and designated HCP-1, HCP-2 and HCP-3, respectively.

Each probe was dissolved at a concentration of 100 pmol/µL in sterilized ultra-pure water and used in the following experiments.

Example 7

1. Procedure

1 µL of a pair of oligonucleotides of HCP-1 (100 pmol/µL), 1 µL of a pair of oligonucleotides of HCP-2 (100 pmol/µL) and 1 µL of a pair of oligonucleotides of HCP-3 (100 pmol/µL) were each added to 0.2 mL tubes, respectively, and 12 µL of 20×SSC and 6 µL of $DW^2$ (sterilized redistilled water) were added to each reaction tube to give a solution with a total volume of 20 µl, which was then mixed by a vortex and spun down.

Five mixed solutions were prepared in this manner from each kind of HCP and reacted "at 94° C. for 10 seconds and at 62° C. for 30 minutes", "at 94° C. for 10 seconds and at 64° C. for 30 minutes", "at 94° C. for 10 seconds and at 66° C. for 30 minutes", "at 94° C. for 10 seconds and at 68° C. for 30 minutes" and "at 94° C. for 10 seconds and at 70° C. for 30 minutes", respectively.

After the reaction, each heated reaction tube was cooled finally to 15° C. and stocked at 4° C. prior to electrophoresis.

10 µL of the reaction solutions were mixed with 2 µL of BPB (Bromothymol Blue) as a staining solution, and those samples were electrophoresed at 100 V for 35 minutes using 0.5% agarose gel (Nusive-3: 1, produced by Takara Co., Ltd.).

2. Results

At the reaction temperature of 62° C., HCP-1 has already initiated polymer formation, while HCP-2 shows a larger amount of ladder products indicating insufficient polymer formation. At the reaction temperature of 62° C., HCP-3 shows a ladder state at a whole lane because of the presence of unspecific bonding.

Figure 33:
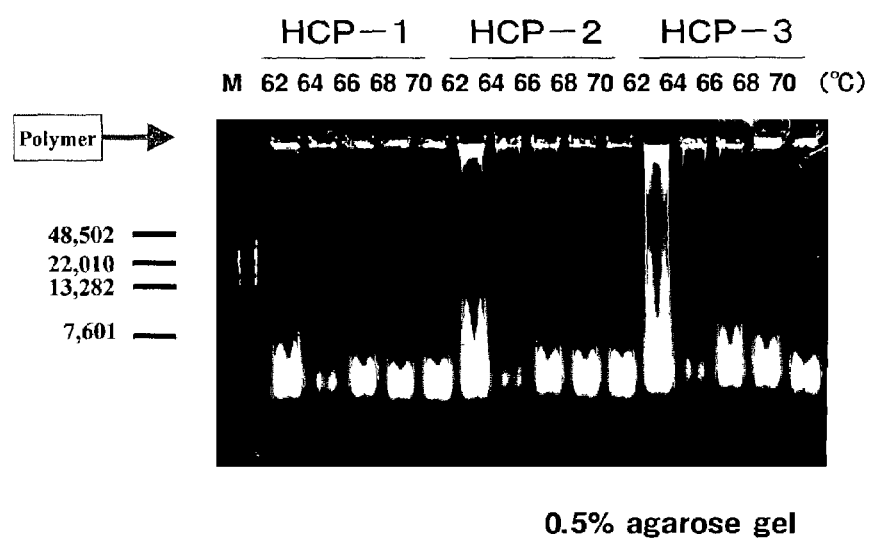
FIG. 33 is a photograph showing the influence of a reaction temperature on formation of a polymer from HCP by the use of the stacking effect.

Accordingly, as shown in the photograph in FIG. 33, it was confirmed that in HCP-1 having both G (guanine)—C (cytosine) bonds as base sequences at two branched sites in each region when hybridizing cross and alternately, a stable double-stranded polymer is formed efficiently at a lower reaction temperature.

Example 8

1. Procedure 1.5 µL of a pair of oligonucleotides of HCP-1 (100 pmol/µL), 1.5 µL of a pair of oligonucleotides of HCP-2 (100 pmol/µL) and 1.5 µL of a pair of oligonucleotides of HCP-3 (100 pmol/μL) were each added to 0.2 mL tubes respectively, and 36 μL of 20×SSC and 21 μL of DW$^2$ were added to each reaction tube to give a solution with a total volume of 60 μL, which was then mixed by a vortex and spun down.

Five mixed solutions were prepared in this manner from each kind of HCP and reacted "at 94° C. for 10 seconds and at 64° C. for 0 hour (on ice)", "at 94° C. for 10 seconds and at 64° C. for 0.5 hour", "at 94° C. for 10 seconds and at 64° C. for 3 hours", "at 94° C. for 10 seconds and at 64° C. for 16 hours" and "at 94° C. for 10 seconds and at 64° C. for 16 hours (vibration)", respectively, to form a polymer.

After the reaction, each heated reaction tube was cooled finally to 15° C. and stocked at 4° C. prior to electrophoresis.

10 μL of the reaction solutions were mixed each with 2 μL of BPB (Bromothymol Blue) as a staining solution, and those samples were electrophoresed at 100 V for 35 minutes using 0.5% agarose gel (Nusive-3: 1, produced by Takara Co., Ltd.).

2. Results

HCP-1 has already initiated polymer formation in the 0.5-hour reaction time, and shows a very low amount of the unreacted probe (bands in a lower part of the lane) in the 3-hour reaction time, thus indicating that the majority of HCP-1 has been consumed in polymer formation. On the other hand, HCP-2 shows a large amount of ladder products and indicates insufficient polymer formation in the 0.5-hour reaction time. Further, HCP-3 does not form any polymer in the 0.5-hour reaction time.

Figure 34:
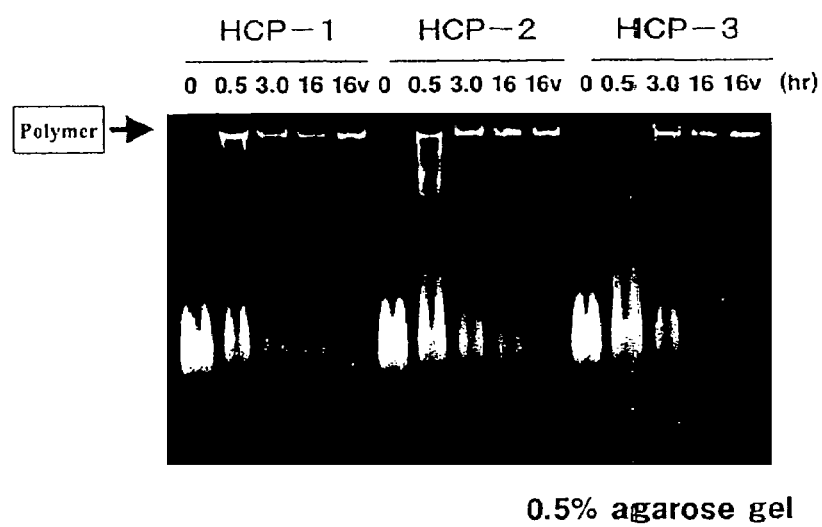
FIG. 34 is a photograph showing the influence of a reaction time on formation of a polymer from HCP by the use of the stacking effect.

Accordingly, as shown in the photograph in FIG. 34, it was confirmed that in HCP-1 having both G (guanine)—C (cytosine) bonds as base sequences at two branched sites in each region when hybridizing alternately, a stable double-stranded polymer is formed efficiently in a shorter reaction time.

Example 9

1. Procedure

2 μL of a pair of oligonucleotides of HCP-1, HCP-2 and HCP-3 were each put to 0.2 mL reaction tubes at oligonucleotide probe concentrations of "10 pmol/μL", "5.0 pmol/μL" and "2.5 pmol/μL", respectively, and 12 μL of 20×SSC and 6 μL of DW$^2$ were added to each tube to give a solution with a total volume 20 μl, which was then mixed by a vortex and spun down.

Those mixed solutions were reacted "at 94° C. for 10 seconds and at 64° C. for 30 minutes".

Thereafter, each reaction solution was lowered finally to 15° C. and stocked at 4° C. prior to electrophoresis.

10 μL of the reaction solutions were mixed each with 2 μL of BPB (Bromothymol Blue) as a staining solution, and those samples were electrophoresed at 100 V for 35 minutes using 0.5% agarose gel (Nusive-3: 1, produced by Takara Co., Ltd.).

2. Results

At the lowest probe concentration of "2.5 pmol/μL", HCP-1 has already initiated polymer formation, while HCP-2 shows ladder products indicating insufficient polymer formation. Further, HCP-3 does not form any polymer at the probe concentration of "2.5 pmol/μL".

Figure 35:
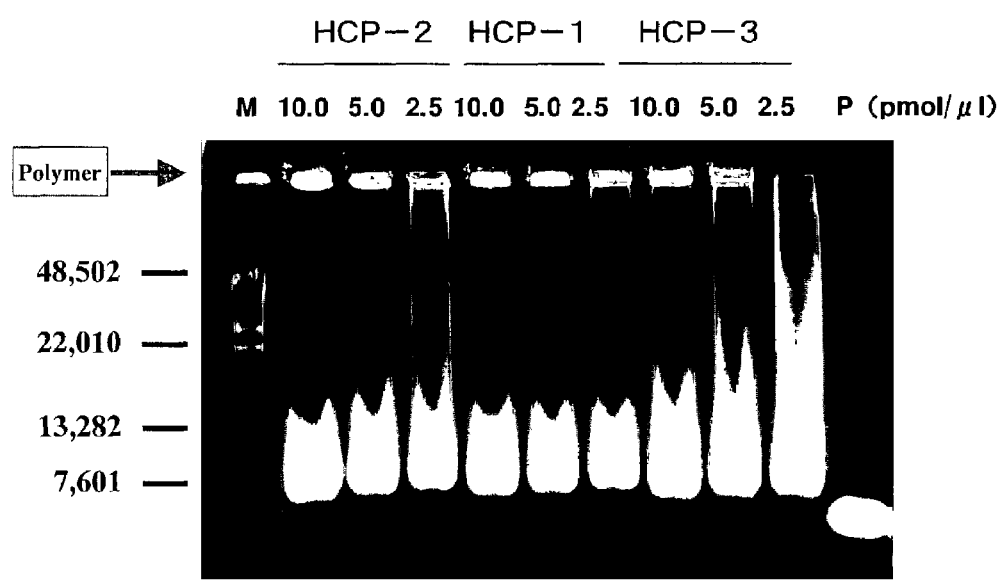
FIG. 35 is a photograph showing the influence of an HCP concentration on formation of a polymer from HCP by the use of the stacking effect.

Accordingly, as shown in the photograph in FIG. 35, it was confirmed that in HCP-1 having both G (guanine)—C (cytosine) bonds as base sequences at two branched sites in each region when hybridizing alternately, a stable double-stranded polymer is formed efficiently at a lower probe concentration.

Example 10

1. Procedure

1 μL of a pair of oligonucleotides of HCP-1, HCP-2 and HCP-3 were put each to 0.2 mL reaction tubes at oligonucleotide probe concentrations of "2.5 pmol/μL" respectively, and 12 μL of 20×SSC and 7 μL of DW$^2$ were added to each tube to give a solution with a total volume 20 μl, which was then mixed by a vortex and spun down.

Those mixed solutions were reacted "at 94° C. for 10 seconds and at 64° C. for 10 minutes".

Thereafter, each reaction solution was lowered finally to 15° C. and stocked at 4° C. prior to electrophoresis.

10 μL of the reaction solutions were mixed each with 2 μL of BPB (Bromothymol Blue) as a staining solution, and those samples were electrophoresed at 100 V for 35 minutes using 0.5% agarose gel (Nusive-3: 1, produced by Takara Co., Ltd.).

2. Results

In the short reaction time of 10 minutes and at the low probe concentration of "2.5 pmol/μL", HCP-1 has already initiated polymer formation, while HCP-2 shows a large amount of ladder products indicating insufficient polymer formation. Further, HCP-3 shows a ladder lane as a whole, failing to form a polymer.

Figure 36:
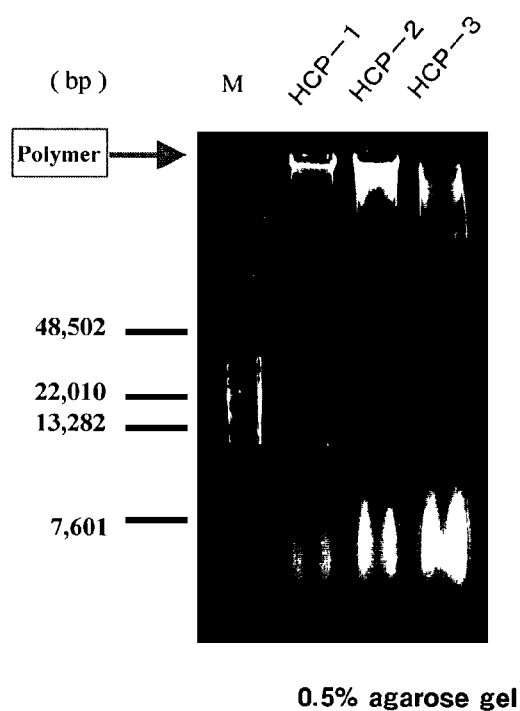
FIG. 36 is a photograph showing the influence of HCP concentration in a short reaction time on formation of a polymer from HCP by the use of the stacking effect.

Accordingly, as shown in the photograph in FIG. 36, it was confirmed that in HCP-1 having both G (guanine)—C (cytosine) bonds as base sequences at two branched sites in each region when hybridizing alternately, a stable double-stranded polymer is formed efficiently even in a short reaction time and at a low probe concentration.

Example 11

1. Procedure 1.5 μL of HCP-1 (100 pmol/μL), HCP-2 (100 pmol/μL) and HCP-3 (100 pmol/μL) were put each to 0.2 mL reaction tubes respectively, and 36 μL of 20×SSC and 21 μL of DW$^2$ were added to each tube to give a solution with a total volume 60 μl, which was then mixed by a vortex and spun down.

Nine mixed solutions were prepared in this manner from each kind of HCP and divided into 3 groups, which were then reacted "at 94° C. for 10 seconds and at 64° C. for 0 hour (on ice)", "at 94° C. for 10 seconds and at 64° C. for 3 hours", "at 94° C. for 10 seconds and at 64° C. for 16 hours" respectively, to form a polymer.

After the reaction at 64° C., each heated reaction was cooled finally to 15° C. and stocked at 4° C. prior to electrophoresis.

After the reaction, the ultraviolet absorption was measured by a spectrophotometer with DW$^2$ as the blank.

2. Results

By changing the reaction time at 64° C., the absorbance at 260 nm in the ultraviolet range was decreased as the reaction time was increased and as the degree of formation of the polymer was increased. This is due to a hypochromic effect called "hypochromism" causing a decrease in the intensity of an absorption band of DNA or an oligonucleotide at 260 nm in the ultraviolet region, which is caused by the fact that the stacking of bases has a regular higher-order structure. Accordingly, the significant reduction in the absorbance of HCP-1 in the ultraviolet range after the reaction "at 94° C. for 10 seconds and at 64° C. for 16 hours" by which a larger number of polymers were formed, indicates the formation of further regular and stabilized higher-order polymer by the use of HCP-1, and concurrently the state of the polymer could be confirmed by the change in the ultraviolet absorption.

Figure 37:
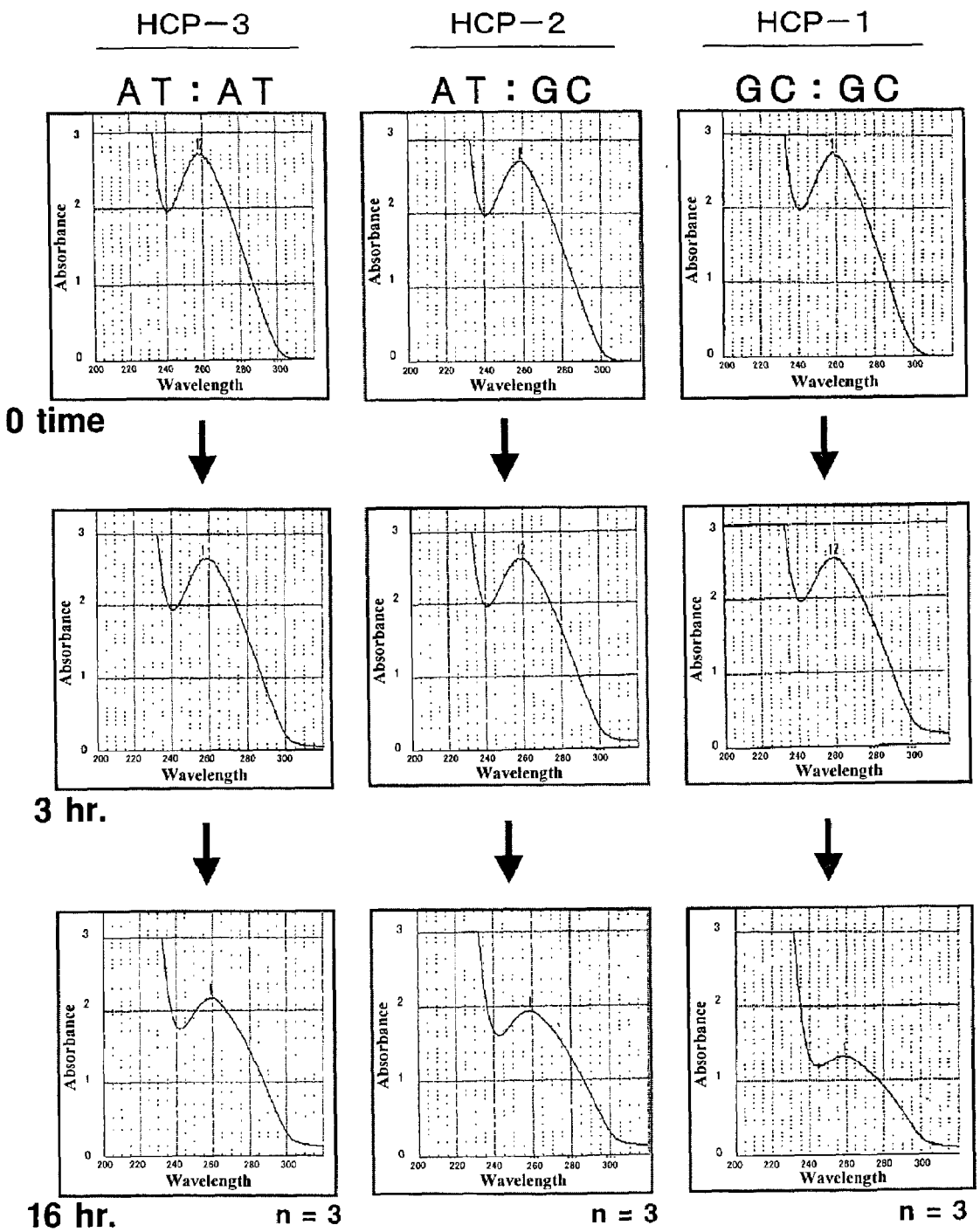
FIG. 37 is a diagram showing a photochemical change of each polymer upon exposure to ultraviolet rays.

Accordingly, the method for detecting the polymer by utilizing the change of the optical absorption of the polymer to ultraviolet rays is demonstrated as shown in FIG. 37.

Example 12

1. Procedure (1) Formation of a Polymer 2.5 µL of HCP-1 (100 pmol/µL), HCP-2 (100 pmol/µL) and HCP-3 (100 pmol/µL), were put each to 0.2 mL reaction tubes respectively, and 60 µL of 20×SSC and 35 µL of $DW^2$ were added to each tube to give a solution with a total volume 100 µl, which was then mixed by a vortex and spun down.

Eighteen mixed solutions were prepared in this manner from each kind of HCP and divided into 6 groups, which were then reacted "at 94° C. for 10 seconds and at 64° C. for 0 hour (on ice)", "at 94° C. for 10 seconds and at 64° C. for 0.5 hour", "at 94° C. for 10 seconds and at 64° C. for 1 hour", "at 94° C. for 10 seconds and at 64° C. for 3 hours", "at 94° C. for 10 seconds and at 64° C. for 5 hours", and "at 94° C. for 10 seconds and at 64° C. for 16 hours", respectively, to form a polymer.

After the reaction at 64° C., each heated reaction was cooled finally to 15° C. and stocked at 4° C.

(2) Staining with SYBR Green I

1 µL of self-fluorescent SYBR Green I (Takara Co., Ltd.) having the property of being inserted into a 3.4 Å space between base-pair planes was dissolved in 10 mL of TE buffer (10 mM, 1 mM, pH 8.0) to prepare a solution diluted at 1/10000. 5 µL of the SYBR Green I solutions (diluted at 1/1000) were added to each tube containing a polymer formed in the above (1), and then mixed by a vortex and spun down.

Each sample was left in a dark room for 1.5 hours to react with the fluorescent material.

2. Results

The tables and graphs in FIG. 38 show that when the reaction time at 64° C. was changed, the higher the degree of formation of a double-stranded chain, the more the fluorescence intensity. This phenomenon appeared in HCP-1 for the shortest time. This indicates that at an early reaction time stage, a double-stranded chain of HCP-1 was formed more efficiently [FIG. 38(a), (b) and (c)].

Accordingly, the state of the polymer could be confirmed by intercalating the fluorescent material SYBR Green I between stacked bases in the formed double-stranded chain.

Example 13

1. Procedure (1) Formation of a Polymer 1.5 µL each of HCP-1 (100 pmol/µL), HCP-2 (100 pmol/µL) and HCP-3 (100 pmol/µL), 36 µL of 20×SSC and 21 µL of $DW^2$ were added each to 0.2 mL reaction tubes to give solutions with total volume 60 µl, which was then mixed by a vortex and spun down.

Sixteen mixed solutions were prepared in this manner from each kind of HCP and divided into 4 groups which were then reacted "at 94° C. for 10 seconds and at 64° C. for 0 hour (on ice)", "at 94° C. for 10 seconds and at 64° C. for 0.5 hour", "at 94° C. for 10 seconds and at 64° C. for 3 hours" and "at 94° C. for 10 seconds and at 64° C. for 16 hours" respectively, to form a polymer.

Out of 4 tubes in each group, 1 tube was used for electrophoresis, and 3 tubes were used at "n=3" for a fluorescence reader.

After the reaction at 64° C., each reaction solution was lowered to 15° C. and stocked at 4° C.

(2) Confirmation by Electrophoresis

10 µL of the reaction solutions were mixed with 2 µL of BPB (Bromothymol Blue) as a staining solution, and those samples were electrophoresed at 100 V for 35 minutes using 0.5% agarose gel (Nusive-3: 1, produced by Takara Co., Ltd.).

(3) Staining with SYBR Green I

1 µL of SYBR Green I (Takara Co., Ltd.) used in Example 12 was dissolved in 0.5 mL of $DW^2$ to prepare a 1/500 dilute solution. 5 µL of this solution (a 1/500 dilute solution) of SYBR Green I (Takara Co., Ltd.) were added to each tube containing the polymer formed in the above (1) and then mixed in a vortex and spun down.

After each tube was left in a dark room for 0.5 to 1 hour to react with the fluorescent material, each sample was transferred to a 1.5 mL tube, precipitated in a usual manner with ethanol and left overnight at −20° C.

After those samples were left overnight, they were returned to room temperature and centrifuged at 12,000 rpm×15 minutes (room temperature), and after the supernatant was removed, the pellet was air-dried, dissolved in 60 µL of $DW^2$ and measured with a fluorescence reader.

2. Results

"SYBR Green I" is a fluorescent dye intercalating between the base pairs of the double-stranded helix of nucleic acids, and the dye bound to nucleic acids can be removed by ethanol precipitation.

Figure 39:
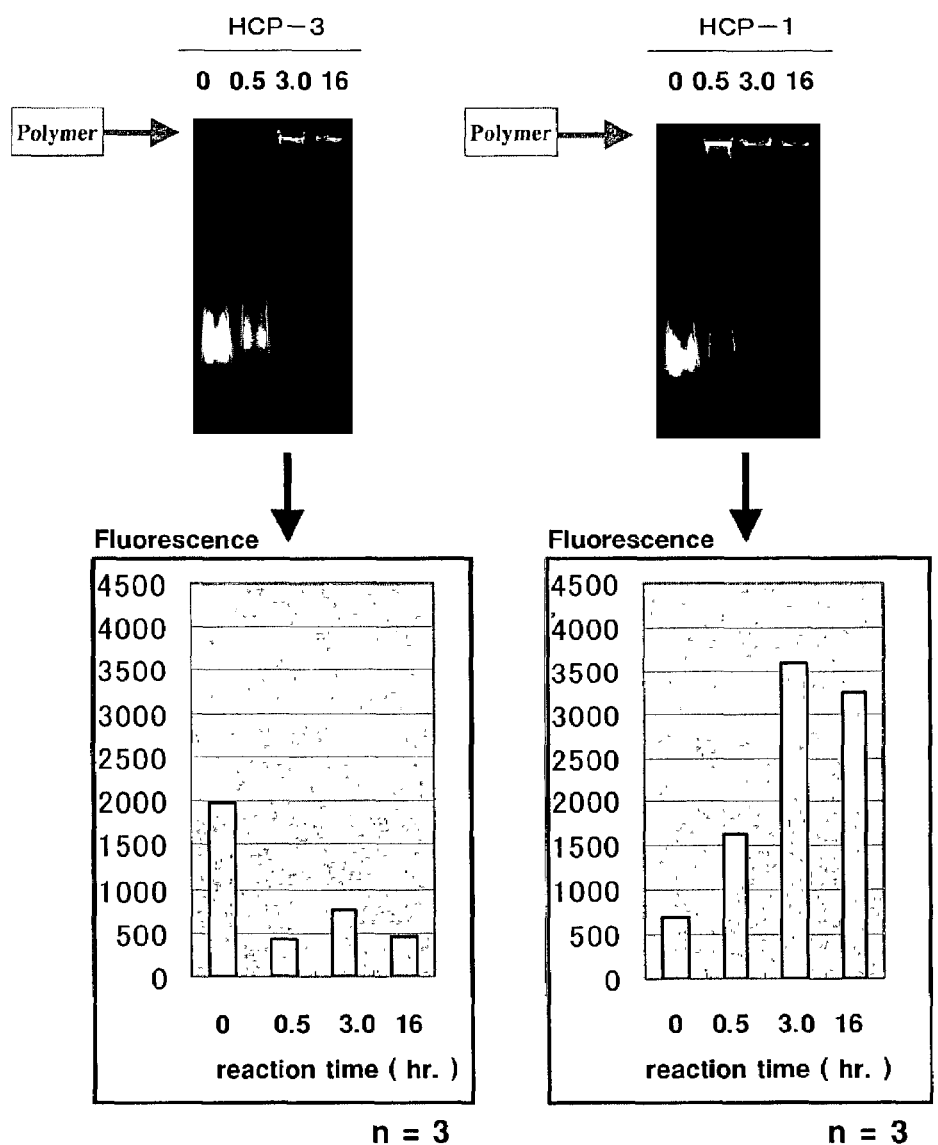
FIG. 39 is a diagram showing cases where each polymer having a fluorescent material intercalated therein and then subjected to purification with EtOH was detected by the photochemical change of the fluorescent material to the polymer.

The data shown in FIG. 38 were obtained by measuring the sample by a fluorescence reader directly without ethanol precipitation, while the data in FIG. 39 were obtained after intercalating of the fluorescent material and subsequent purification of the polymer by ethanol precipitation.

FIG. 39 shows that when the reaction time at 64° C. was changed, the higher the degree of formation of the polymer, the more the fluorescence intensity in HCP-1. This indicates that because the polymer of HCP-1 has a regular higher-order structure, the fluorescent material is hardly removable therefrom even by ethanol precipitation, and as the degree of formation of the polymer is increased, a further higher-order structure is formed to make the fluorescent material further hardly removable therefrom.

On one hand, the fluorescence intensity of HCP-3 did not depend on the reaction time. This indicates that HCP-3 forms an irregular polymer having a single strand partially in place of a double strand, so that after intercalating of the fluorescent material and subsequent precipitation with ethanol, the polymer is in such an instable state that the fluorescent material is easily removable.

It was thus demonstrated that after permitting the fluorescent material to intercalate in the polymer and purifying the polymer with ethanol, the state of the polymer can be confirmed by measurement thereof by a fluorescence reader.

Capability of Exploitation in Industry

According to the present invention as described above, a stable probe-polymer can be produced by strengthening the bond strength between base pairs at branched sites in each region, a target gene can be detected efficiently without using DNA polymerase or branched DNA, and further the stacking of bases in the formed polymer has a regular higher-order structure bringing about a hypochromic effect called "hypochromism" reducing the intensity of an absorption band at 260 nm in the ultraviolet region, whereby the state of the polymer can be confirmed, and furthermore an inexpensive fluorescent material can be inserted between stacked bases of the polymer to cause a change in fluorescence intensity, whereby the state of the polymer can be confirmed, thus demonstrating the significant effect that a target gene can be detected easily at unprecedented low cost.

The invention claimed is:

1. Probes for forming a probe-polymer comprising a first probe and a second probe having the following characteristics (a), (b), (c), and (d):
   (a) the first and second probes each comprising n base sequence regions complementary to each other, wherein an $X_1$ region, an $X_2$ region, an $X_3$ region, ... an $X_n$ region provided in this order from the 5'-terminal of the first probe have base sequences complementary respectively to an $X_1'$ region, an $X_2'$ region, an $X_3'$ region, ... an $X_n'$ region provided in this order from the 5' terminal of the second probe, wherein n is at least 3;
   (b) when the first and second probes are reacted with each other, the $X_1$ region hybridizes only to the $X_1'$ region, the $X_2$ region hybridizes only to the $X_2'$ region, the $X_3$ region hybridizes only to the $X_3'$ region, ... and the $X_n$ region hybridizes only to the $X_n'$ region, and when both the probes are bound, they hybridize to each other at any one of the regions in one probe, and a plurality of the first and second probes bound at the one region hybridize to each other to form a probe-polymer;
   (c) at least one G (guanine) or C (cytosine) is arranged at both terminals of each one of the complementary base sequence regions in the first and second probes, and upon hybridization of the first and second probes, at least one C—G bond is formed at all of the terminals of the complementary regions; and
   (d) the number of bases in each complementary base sequence region in the first and second probes is at least 8.

2. The probes for forming a probe-polymer according to claim 1, wherein the number (n) of complementary base sequence regions in the first and second probes is 3, 4, 5, or 6.

3. The probes for forming a probe-polymer according to claim 1 or 2, wherein the first and second probes comprise bases selected from DNA, RNA, or PNA.

4. A reagent for detecting a target gene in a sample, comprising a first probe and a second probe as polymerization probes having the following characteristics (a), (b), (c), (d), and (e) as essential elements:
   (a) the first and second probes each comprising n base sequence regions complementary to each other, wherein an $X_1$ region, an $X_2$ region, an $X_3$ region, ... an $X_n$ region provided in this order from the 5'-terminal of the first probe have base sequences complementary respectively to an $X_1'$ region, an $X_2'$ region, an $X_3'$ region, ... an $X_n'$ region provided in this order from the 5' terminal of the second probe, wherein n is at least 3;
   (b) when the first and second probes are reacted with each other, the $X_1$ region hybridizes only to the $X_1'$ region, the $X_2$ region hybridizes only to the $X_2'$ region, the $X_3$ region hybridizes only to the $X_3'$ region, ... and the $X_n$ region hybridizes only to the $X_n'$ region, and when both the probes are bound, they hybridize to each other at any one of the regions in one probe, and a plurality of the first and second probes bound at the one region hybridize to each other to form a probe-polymer;
   (c) at least one G (guanine) or C (cytosine) is arranged at both terminals of each one of the complementary base sequence regions in the first and second probes, and upon hybridization of the first and second probes, at least one C—G bond is formed at all of the terminals of the complementary regions;
   (d) one of the complementary base sequence regions in either one of the first or second probe has a region having a base sequence complementary to a part of the target gene; and (e) the number of bases in each complementary base sequence region in the first and second probes is at least 8.

5. A reagent for detecting a target gene in a sample, comprising: a first and a second probe having the following characteristics (a), (b), (c), and (d) as polymerization probes; and at least one target gene capture probe comprising at least two regions, one region of which is a base sequence region complementary to a part of the target gene and the other region of which is a base sequence region complementary to one region in either one of the two polymerization probes as essential elements, (a) the first and second probes each comprising n base sequence regions complementary to each other, wherein an $X_1$ region, an $X_2$ region, an $X_3$ region, ... an $X_n$ region provided in this order from the 5'-terminal of the first probe have base sequences complementary respectively to an $X_1'$ region, an $X_2'$ region, an $X_3'$ region, ... an $X_n'$ region provided in this order from the 5' terminal of the second probe, wherein n is at least 3;

(b) when the first and second probes are reacted with each other, the $X_1$ region hybridizes only to the $X_1'$ region, the $X_2$ region hybridizes only to the $X_2'$ region, the $X_3$ region hybridizes only to the $X_3'$ region, ... and the $X_n$ region hybridizes only to the $X_n'$ region, and when both the probes are bound, they hybridize to each other at any one of the regions in one probe, and a plurality of the first and second probes bound at the one region hybridize to each other to form a probe-polymer;

(c) at least one G (guanine) or C (cytosine) is arranged at both terminals of each one of the complementary base sequence regions in the first and second probes, and upon hybridization of the first and second probes, at least one C—G bond is formed at all of the terminals of the complementary regions; and (d) the number of bases in each complementary base sequence region in the first and second probes is at least 8.

6. The reagent for detecting a target gene according to claim 4 or 5, wherein the number (n) of complementary base sequence regions in the first and second probes is 3, 4, 5, or 6.

7. The reagent for detecting a target gene according to claim 4 or 5, wherein the first and second probes comprise bases selected from DNA, RNA, or PNA.

* * * * *

UNITED STATES PATENT AND TRADEMARK OFFICE
CERTIFICATE OF CORRECTION

PATENT NO. : 7,060,814 B2  Page 1 of 1
APPLICATION NO. : 09/979999
DATED : June 13, 2006
INVENTOR(S) : Mitsugu Usui et al.

It is certified that error appears in the above-identified patent and that said Letters Patent is hereby corrected as shown below:

On Title Page, Col. 1

In the Title, in item (54):

Please replace "PROBE FOR CONSTRUCTING PROBE-POLYMER METHOD OF CONSTRUCTING PROBE-POLYMER AND UTILIZATION THEREOF" with -- PROBE-POLYMER FORMING PROBES, METHOD FOR FORMING PROBE-POLYMER, AND USE THEREOF --.

In item (22):

Please replace "May 28, 2001" with -- March 28, 2001 --.

Signed and Sealed this

Twenty-sixth Day of September, 2006

JON W. DUDAS
*Director of the United States Patent and Trademark Office*

UNITED STATES PATENT AND TRADEMARK OFFICE
CERTIFICATE OF CORRECTION

PATENT NO. : 7,060,814 B2  
APPLICATION NO. : 09/979999  
DATED : June 13, 2006  
INVENTOR(S) : Mitsugu Usui et al.

It is certified that error appears in the above-identified patent and that said Letters Patent is hereby corrected as shown below:

TITLE PAGE

Section (30), Foreign Application Priority Data, "March 31, 2000(JP) 2000-098797" should read -- March 31, 2000(JP) 2000-098797 and October 10, 2000(JP) 2000-309959 --.

Signed and Sealed this

Eighth Day of September, 2009

David J. Kappos  
*Director of the United States Patent and Trademark Office*